US012599624B2

(12) United States Patent (10) Patent No.: US 12,599,624 B2
Ghodbane et al. (45) Date of Patent: *Apr. 14, 2026

(54) BIODEGRADABLE LUNG SEALANTS

(71) Applicant: Ethicon, Inc., Raritan, NJ (US)

(72) Inventors: Salim A. Ghodbane, Piscataway, NJ (US); Sridevi Dhanaraj, Branchburg, NJ (US); Brian Aitken, Somerville, NJ (US)

(73) Assignee: Ethicon, Inc., Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/898,897

(22) Filed: Aug. 30, 2022

(65) Prior Publication Data

US 2024/0066052 A1 Feb. 29, 2024

(51) Int. Cl.
| | | |
|---|---|---|
| *A61K 31/787* | (2006.01) | |
| *A61K 31/785* | (2006.01) | |
| *A61K 47/22* | (2006.01) | |
| *A61P 11/00* | (2006.01) | |

(52) U.S. Cl.
CPC .......... *A61K 31/787* (2013.01); *A61K 31/785* (2013.01); *A61K 47/22* (2013.01); *A61P 11/00* (2018.01)

(58) Field of Classification Search
CPC .... A61K 31/787; A61K 31/785; A61K 47/22; A61P 11/00
See application file for complete search history.

(56) References Cited

U.S. PATENT DOCUMENTS

| | | | |
|---|---|---|---|
| 5,583,114 A | 12/1996 | Barrows et al. | |
| 6,371,975 B2 | 4/2002 | Cruise et al. | |
| 6,458,147 B1 * | 10/2002 | Cruise .............. | A61B 17/00491 |
| | | | 606/214 |

(Continued)

FOREIGN PATENT DOCUMENTS

| | | |
|---|---|---|
| CN | 1102911493 A | 2/2013 |
| CN | 105778124 A | 7/2016 |

(Continued)

OTHER PUBLICATIONS

Bouten et al, "The chemistry of tissue adhesive materials", Progress in Polymer Science, vol. 39, Issue 7, pp. 1375-1405 (2014). Retrieved from https://www.sciencedirect.com/science/article/pii/S0079670014000215 (Year: 2014).*

(Continued)

*Primary Examiner* — Marianne C Seidel
*Assistant Examiner* — Joshua A Atkinson
(74) *Attorney, Agent, or Firm* — David R. Crichton

(57) ABSTRACT

The invention relates to a rapid setting liquid lung sealant that forms a highly adherent and elastic hydrogel. Provided are lung sealants comprising two high molecular weight (20 kDa) multi-arm PEG compositions wherein the first PEG composition includes an alkaline buffer and the second PEG composition includes a mildly acidic buffer for optimized set up time and extended working time. In some embodiments, the PEGs further comprise a radioprotectant such as tocopherol. In some embodiments, a colorant is added to one or both PEGs of the lung sealant to improve visualization of the lung sealant against human lung tissue.

22 Claims, 28 Drawing Sheets

(56) References Cited

U.S. PATENT DOCUMENTS

| | | | |
|---|---|---|---|
| 6,605,667 B1 | 8/2003 | Badejo et al. | |
| 6,656,496 B1 | 12/2003 | Kilpadi et al. | |
| 8,133,504 B2 | 3/2012 | Kettlewell et al. | |
| 8,846,849 B2 | 9/2014 | Bordoloi et al. | |
| 8,987,339 B2 * | 3/2015 | Askari | A61L 26/008 |
| | | | 524/879 |
| 10,980,913 B2 | 4/2021 | Dhanaraj et al. | |
| 11,823,028 B2 | 11/2023 | Nativ et al. | |
| 2002/0143276 A1 | 10/2002 | Ernst | |
| 2004/0225077 A1 * | 11/2004 | Gravett | A61P 43/00 |
| | | | 525/523 |
| 2005/0079999 A1 | 4/2005 | Wilkie et al. | |
| 2006/0147409 A1 | 7/2006 | Pathak et al. | |
| 2011/0104280 A1 | 5/2011 | Hnojewyj | |
| 2013/0116341 A1 * | 5/2013 | Askari | A61K 49/04 |
| | | | 524/879 |
| 2015/0352246 A1 | 12/2015 | Henise et al. | |
| 2018/0200403 A1 | 7/2018 | Chang et al. | |
| 2019/0269818 A1 | 9/2019 | Dhanaraj et al. | |
| 2019/0269819 A1 * | 9/2019 | Dhanaraj | A61L 24/02 |
| 2020/0247101 A1 | 8/2020 | Shen et al. | |
| 2021/0205501 A1 * | 7/2021 | Bright | C08L 71/02 |
| 2022/0331475 A1 | 10/2022 | Nativ et al. | |

FOREIGN PATENT DOCUMENTS

| | | | | |
|---|---|---|---|---|
| CN | 106750249 A * | 5/2017 | | A61L 24/0031 |
| CN | 108159483 A | 6/2018 | | |
| CN | 113521376 A | 10/2021 | | |
| WO | 2021250548 A1 | 12/2021 | | |

OTHER PUBLICATIONS

AAT Bioquest, Phosphate Buffer Preparation and Recipe, retrieved Mar. 9, 2024. (Year: 2024).*

Electron Microscopy Sciences, "Acetate Buffer pH 3.6-5.6", retrieved 2024 from https://www.emsdiasum.com/acetate-buffer (Year: 2024).*

Ehterami et al, "Chitosan/alginate hydrogels containing Alpha-tocopherol for wound healing in rate model", Jour. Drug Del. Sci. Tech, 2019, 51, pp. 204-213 (Year: 2019).*

International Search Report & Written Opinion for corresponding PCT Application No. PCT/IB2023/058200, dated Nov. 20, 2023.

Chinese Search Report for corresponding CN Application No. 202211660574.5, dated Oct. 24, 2023.

Appenroth et al., "Protective effects of vitamin E and C on cisplatin nephrotoxicity in developing rat", Arch Toxicol, vol. 71, No. 11, pp. 677-683, 1997.

Miller et al., "Mechanisms of Cisplatin Nephrotoxicity", Toxins, vol. 2, pp. 2490-2518, 2010.

Shi et al., "Cisplatin nephrotoxicity as a model of chronic kidney disease", Lab Invest., vol. 98, No. 8, Aug. 2018.

* cited by examiner

Contour Plot of Average Max Load vs r, PC

Individual Value Plot of Percent Elongation (%)
95% CI for the Mean

FIG. 15

Individual Value Plot of Burst Pressure (mmHg)
95% CI for the Mean

BIODEGRADABLE LUNG SEALANTS

FIELD OF THE INVENTION

The invention relates to two component biodegradable sealants for sealing lung tissue, and methods of use thereof.

BACKGROUND

Tissue sealants are used as an adjunct to primary lung pleura closure with, for example, sutures, surgical meshes, and staples. There is currently no adjunctive hemostatic sealant adopted as the standard of care for lung sealing. PROGEL™ hydrogel (Becton, Dickinson and Company, Franklin Lakes, New Jersey) is the only approved lung sealant in the United States. However, PROGEL™ hydrogel has not been heavily adopted due to its high stiffness which results in a compliance mismatch with the underlying lung tissue. The ensuing shear stress of the sealant-tissue interface ultimately leads to undesirable delamination. Moreover, PROGEL™ hydrogel's low elongation at failure results in an inability to apply the sealant in a fully deflated state. Therefore, PROGEL™ hydrogel must be applied on the lung in a partially inflated state which adds complexity to the application process. The PROGEL™ hydrogel formulation does not set quickly leading to undesired runniness, ultimately, resulting in poor coverage of the targeted lung surface and significant wasted material. Moreover, poor visualization due to the minimal contrast of the sealant on the lung surface can lead to inadequate coverage.

In the Asia-Pacific region, NEOVEIL (Gunze Limited, Tokyo, Japan), a bioabsorbable polyglycolic acid (PGA) sheet for reinforcing sutures and staples, is utilized in conjunction with fibrin sealants for sealing lung tissue. However, NEOVEIL and fibrin sealants have a lower adhesive strength than synthetic sealants. The lower adhesive strength and low elongation at failure can result in undesirable delamination of the NEOVEIL mesh and fibrin sealant from the target tissue.

Lung sealants are used to prevent air leakage after lung surgery or injury. Lung sealants are particularly important for preventing complications such as prolonged alveolar air leak (PAL) after lung surgery, and infections. However, sealing lung tissue is particularly challenging due to the movement of the lungs during respiration. There is a need for a lung sealant having a high tensile strength, high elongation at failure, and a low elastic modulus that does not hinder the natural cyclic movement of the lung.

SUMMARY

The present invention addresses the limitations of currently existing biodegradable sealants. Provided herein are synthetic, biodegradable, two component, rapid setting liquid sealant compositions that form highly adherent and elastic hydrogels. The sealants provided herein have high tensile strength, high elongation at failure, and a low elastic modulus, and are particularly useful as lung sealants that do not hinder the natural cyclic movement of the lung.

Minimizing the stiffness of the lung sealants of the present invention provides unexpected advantageous lung sealing performance. The lung sealants provided herein have reduced stiffness and greater elongation at failure in contrast with sealants currently used for lung sealing. The stiffness of the lung sealants provided herein have about 2.9× lower stiffness, and have an elongation at failure about 7× greater than PROGEL™ hydrogel sealant.

In one embodiment of the present invention, the sealant comprises a two component, flowable, rapid setting, liquid composition that forms a highly adherent and elastic biodegradable hydrogel.

In some embodiments, methods of making the lung sealant compositions of the present disclosure comprise dissolving a first polyethylene glycol (PEG) polymer powder in an alkaline buffer to form a first component, and dissolving a second PEG polymer powder in a mildly acidic buffer to form a second component, wherein the two components are mixed immediately before or during application to a tissue or wound.

In some aspects, methods of making the lung sealants herein comprise: mixing an alkaline buffer with a 4-arm PEG-NH2-HCl containing tocopherol to form a 4-arm PEG-NH2-HCl composition; separately mixing a mildly acidic buffer with a 4-arm PEG-SG containing tocopherol to form a 4-arm PEG-SG composition; simultaneously delivering the 4-arm PEG-NH2-HCl and 4-arm PEG-SG compositions with an applicator device that provides adequate mixing of the 4-arm PEG-NH2-HCl and 4-arm PEG-SG compositions onto a lung tissue; and allowing the lung sealant to cure on the lung tissue.

In a preferred embodiment, the lung sealant composition is composed of two high molecular weight (20 kDa) 4-arm PEG polymers wherein one PEG is dissolved in an alkaline buffer and the other PEG is dissolved in a mildly acidic buffer, for optimized preparation time and extended working time before curing or gelation.

In some aspects, the biodegradable lung sealants comprise a first component comprising a first multi-arm PEG and an alkaline buffer for reconstituting the first multi-arm PEG; and a second component comprising a second multi-arm PEG and a mildly acidic buffer for reconstituting the second multi-arm PEG; wherein when the first and second components are combined they produce an adherent and elastic biodegradable lung sealant.

In some embodiments, the flowable sealants of the present invention comprise a two-component composition wherein the two components are mixed immediately before or during application to a tissue or wound, and wherein the first component comprises a multi-arm PEG-Amine (PEG-NH2) and the second component comprises a multi-arm PEG-succinimidyl glutarate (PEG-SG). In some preferred embodiments, the first component of the sealant composition comprises 4-arm PEG-Amine HCl salt (4-arm PEG-NH2-HCl) 20 kDa and the second component comprises 4-arm PEG-succinimidyl glutarate (4-arm PEG-SG) 20 kDa.

In a preferred embodiment, a 4-arm PEG-Amine 20 kDa is combined with an alkaline N-cyclohexyl-2-aminoethanesulfonic acid (CHES) buffer to form a first component of the sealant composition, and a 4-arm PEG-SG 20 kDa is combined with a mildly acidic citrate buffer to form a second component of the sealant composition.

In some embodiments, the first and second components are delivered to lung tissue with a device that provides adequate mixing of the components.

In some embodiments of the present disclosure, the PEG polymer comprises a free radical scavenger to neutralize reactive oxygen species (ROS). In some aspects, the free radical scavenger is a radioprotectant which improves the robustness of the sealant composition to irradiation. In aspects, the radioprotectant is an antioxidant such as tocopherol. Examples of suitable tocopherols are α-tocopherol, β-tocopherol, γ-tocopherol, δ-tocopherol, tocotrienol, and combinations thereof. In preferred embodiments, the radioprotectant is compounded into the PEG powder before adding buffer to the PEG powder.

In some embodiments, the sealant compositions further comprise a colorant to improve the visualization of the sealant against human tissue and allow for more consistent coverage of the targeted tissue. In some preferred embodiments, one or more colorants is compounded with a PEG powder. In some aspects of the present invention, the colorant is FD&C Blue #1.

In some preferred embodiments, about 730 ppm to about 3000 ppm FD&C Blue #1 is added to PEG-Amine powder, PEG-SG powder, or both the PEG-Amine and PEG-SG powders. More preferably, about 1000 ppm to about 1600 ppm FD&C Blue #1 is added to PEG-Amine powder, PEG-SG powder, or both the PEG-Amine and PEG-SG powders.

In some aspects, the PEG powder for preparing a component of the lung sealants of the invention includes both a first additive and a second additive wherein the first additive is a radioprotectant, such as an antioxidant, and the second additive is a colorant. In one embodiment, the first additive is tocopherol and the second additive is FD&C Blue #1.

In one aspect, all of the components of the sealants and kits of the present disclosure, including the PEG powders, buffers, solutions, and containers, are sterilized starting with at least a minimally effective X-ray irradiation dose, and most preferably, up to about 39 kiloGrays (kGy) or up to about 47 kGy.

In another embodiment of the sealant, each of the PEG-SG and/or PEG-Amine is mixed with about 500 to about 4000 ppm tocopherol. In a preferred embodiment, about 1500 to about 3000 ppm of tocopherol is added to each of the PEGs.

In some embodiments, the PEG-SG and PEG-Amine each have equal molecular weights. In a preferred embodiment, the PEG-SG and PEG-Amine each have molecular weights of about 20 kDa.

In another embodiment, each of the PEG-SG and PEG-Amine final concentrations in the sealant applied to a tissue are about 39 mg/mL to about 87 mg/mL, preferably about 52 mg/mL to about 77 mg/mL and, more preferably, 67 mg/mL.

In some embodiments, at least a portion of each of the multi-arm PEGs prior to dissolution is present in a form of particles having a size greater than or equal to about 250 microns. In another aspect, the range of particle size of the at least one multi-arm PEG is about 250 to about 1250 microns.

In another aspect, the PEG-Amine has about 20% particles having a size of at least 710 μm to maximize the dissolution rate and minimize preparation time of the sealant.

In another aspect, the PEG-SG has about 40% particles having a size of at least 500 μm to maximize the dissolution rate and minimize preparation time of the sealant.

In another embodiment, the pKa of the reconstitution buffer for PEG-Amine is preferably about 8.0 to about 9.7 pKa, and most preferably about 8.8 to about 9.4 pKa.

In another embodiment, the pH of the reconstitution buffer for PEG-Amine is at least 0.05 pH units above the buffer pKa.

In another aspect of the sealants provided herein, the PEG-Amine/CHES solution after reconstitution has a preferred pH of about 9.0 to about 10.5, and more preferably about 9.20 to about 9.80. In a most preferred embodiment, the PEG-Amine/CHES solution has a pH after reconstitution of about 9.35.

In another embodiment, the reconstitution buffer for PEG-Amine in a prefilled device is about 190 to about 210 mM CHES buffer with a pH prior to reconstitution of preferably about 9.34 to about 9.80.

In another aspect, the reconstitution buffer for PEG-Amine in a prefilled device is about 180 mM to about 220 mM CHES buffer having a pH prior to reconstitution of about 9.35 to about 9.80.

In another embodiment, the reconstitution buffer for PEG-Amine in a prefilled device is from about 180 to about 220 mM CHES buffer having a pH prior to reconstitution of about 9.37 to about 9.80.

In a preferred embodiment, the reconstitution buffer for PEG-Amine in a prefilled device is 200 mM CHES buffer having a pH prior to reconstitution of 9.58.

In another embodiment, the reconstitution buffer for PEG-SG is a citrate buffer having an initial pH of ≤7.0 and a concentration of about 3.5 mM to about 15 mM, and more preferably, about 5.5 mM to about 12.5 mM.

In a preferred embodiment, before irradiation, the concentration of the citrate buffer is 9.04 mM and the initial pH is about 4.5.

In another embodiment, the colorant, such as FD&C Blue #1, is compounded into one or both dry PEG powders. In another aspect, FD&C Blue #1 is compounded into one or both of the PEG powders at a concentration of about 730 ppm to about 3000 ppm before irradiation.

In another embodiment of the device, FD&C Blue #1 is increased by up to 300 ppm to account for irradiation induced loss of color. Preferably, the final concentration of the FD&C Blue #1 in the lung sealants of the invention is about 50 ug/mL to about 100 ug/mL.

In a preferred embodiment, the lung sealant comprises two 4-arm PEGs wherein the first PEG is a 4-arm PEG-NH2-HCl and the second PEG is 4-arm PEG-SG, the alkaline buffer is CHES, the mildly acidic buffer is citrate buffer, the antioxidant is tocopherol and the colorant is FD&C Blue #1, and wherein the final concentration of the lung sealant composition after combining the components is 67 mg/mL 4-arm PEG-SG (20 kDa), 67 mg/mL 4-arm PEG-NH2-HCl (20 kDa), 100 mM CHES, 4.5 mM citrate buffer, 340 μg/mL tocopherol, and 88 ug/mL FD&C Blue #1.

In some embodiments of the present invention, kits are provided wherein each kit comprises two dry PEG powders and two buffers. In a preferred embodiment the kit includes dry 4-arm PEG-Amine and dry 4-arm PEG-SG, an alkaline buffer, and mildly acidic buffer.

In another embodiment, the biodegradable sealant is combined with contrast agents for localizing the sealed site at a later time. In one aspect, the contrast agent is a non-ionic contrast agent, such as iohexol, for radiopacity.

In another aspect, the biodegradable sealant is combined with a contrast agent to facilitate detection by magnetic resonance imaging.

In still another embodiment, the contrast agent is a radioactive agent which allows for localization of the sealed site using radiation detection methods.

In another embodiment, the biodegradable sealant composition can be combined with therapeutic agents to provide localized delivery of the therapeutic agent. For example, the therapeutic agents can be one or more chemotherapeutic agents for management of cancer.

In another embodiment, a method of using the lung sealant comprises: adding tocopherol to 4-arm PEG-Amine to form a 4-arm PEG-Amine and tocopherol mixture; irradiating the 4-arm PEG-Amine and tocopherol mixture; adding an alkaline buffer to the 4-arm PEG-Amine and tocopherol mixture to form a first component of the lung sealant; adding tocopherol to 4-arm PEG-NHS ester to form a 4-arm PEG-NHS ester and tocopherol mixture; irradiating the 4-arm PEG-NHS ester and tocopherol mixture; adding a mildly acidic buffer to the 4-arm PEG-NHS ester and tocopherol mixture to form a second component of the lung sealant; and using an applicator device to mix and simultaneously apply the first component and second component onto a lung tissue to form the lung sealant, and allowing the sealant to cure on the tissue.

In some aspects, in the methods of using the lung sealants herein, the 4-arm PEG-Amine and 4-arm PEG-NHS ester are each in the form of a dry powder.

In another aspect, the 4-arm PEG-Amine and tocopherol mixture, and 4-arm PEG-NHS ester and tocopherol mixture are each irradiated with X-ray irradiation up to about 40 kiloGrays (kGy).

As used herein, the terms "comprising", "including", "having" and grammatical variants thereof are to be taken as specifying the stated features, integers, steps or components, but do not preclude the addition of one or more additional features, integers, steps, components or groups thereof. These terms encompass the terms "consisting of" and "consisting essentially of". Moreover, as used herein, the indefinite articles "a" and "an" mean "at least one" or "one or more" unless the context clearly dictates otherwise.

These and other aspects and advantages of the present invention will become more apparent from the following description and accompanying figures.

6

150 mg/mL Human Serum Albumin, 50 mM carbonate (pH=9.0)). The stiffness of the two PEG candidates of the invention was 2.9× lower than Mock PROGEL™ hydrogel.

Figure 7:
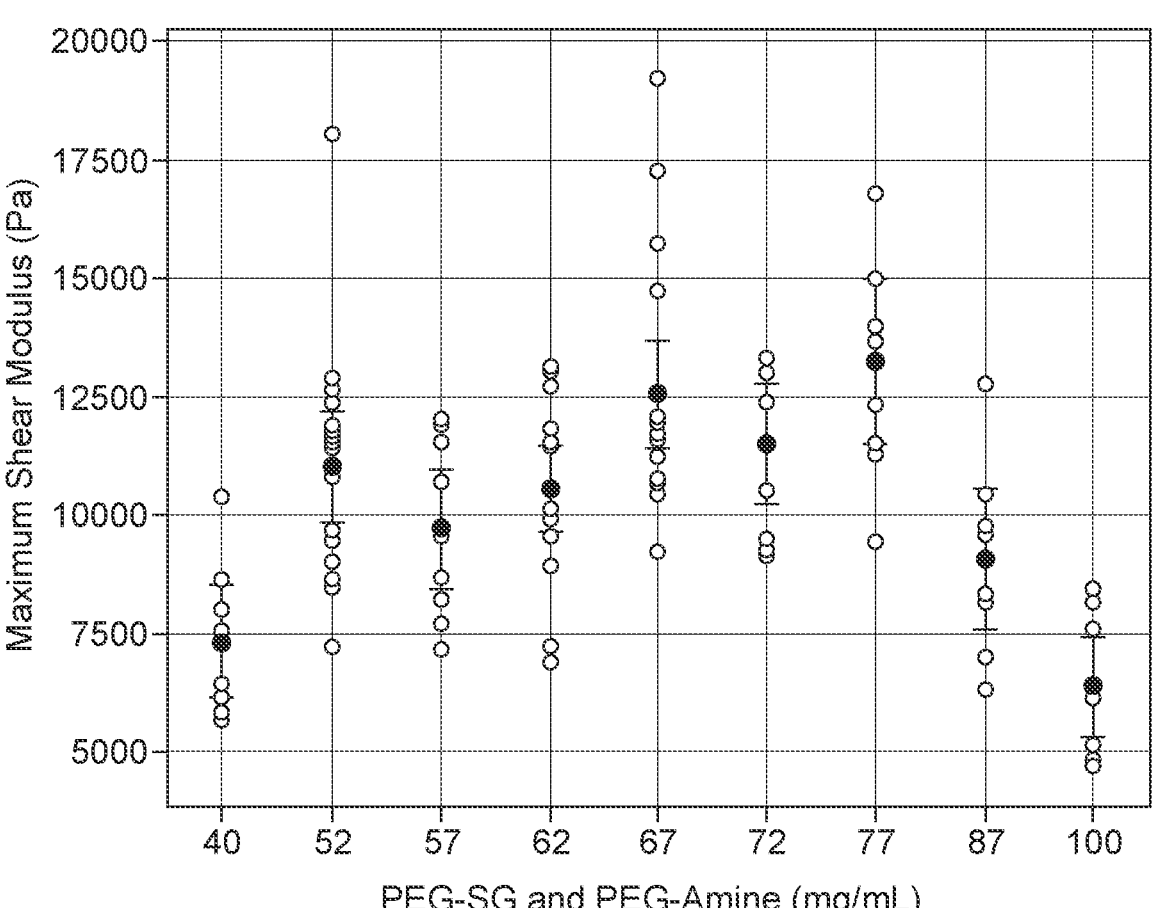

FIG. 7 is a graph of the maximum shear modulus (Pa) of the lung sealants at increasing concentrations of PEG-SG and PEG-Amine in equal ratio from 40 mg/mL to 100 mg/mL.

Figure 8:
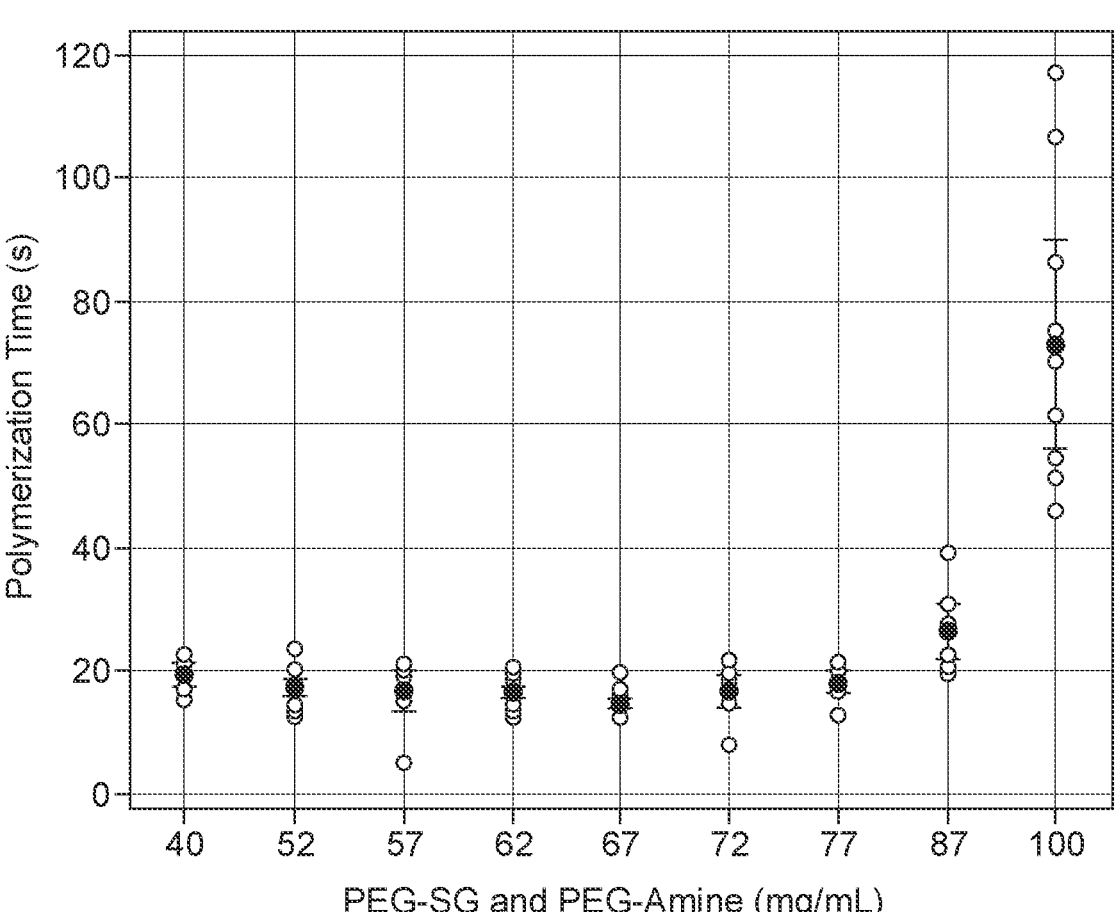

FIG. 8 is a graph showing the polymerization time of the lung sealants at increasing concentrations of PEG-SG and PEG-Amine in equal ratio from 40 mg/mL to 100 mg/mL.

Figure 9:
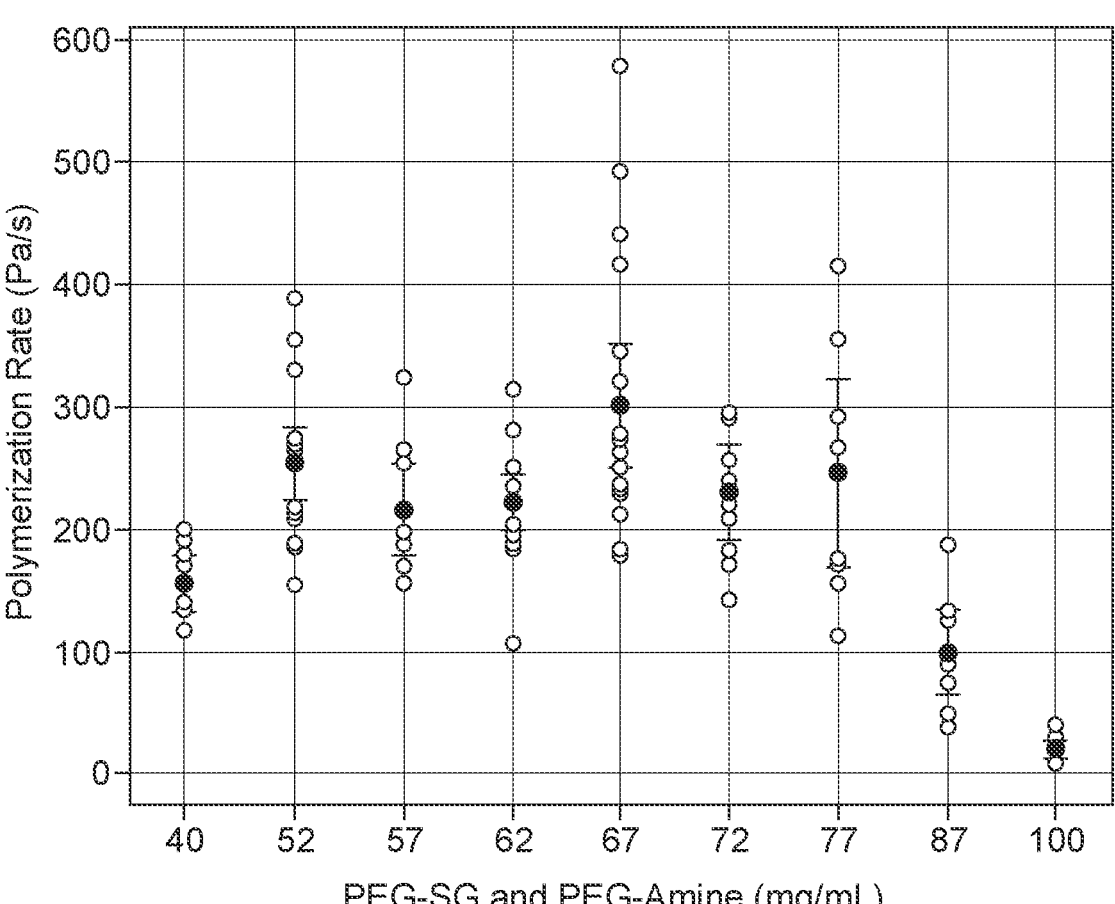

FIG. 9 is a graph showing the polymerization rate of the lung sealants at increasing concentrations of PEG-SG and PEG-Amine in equal ratio from 40 mg/mL to 100 mg/mL.

Figure 10A:
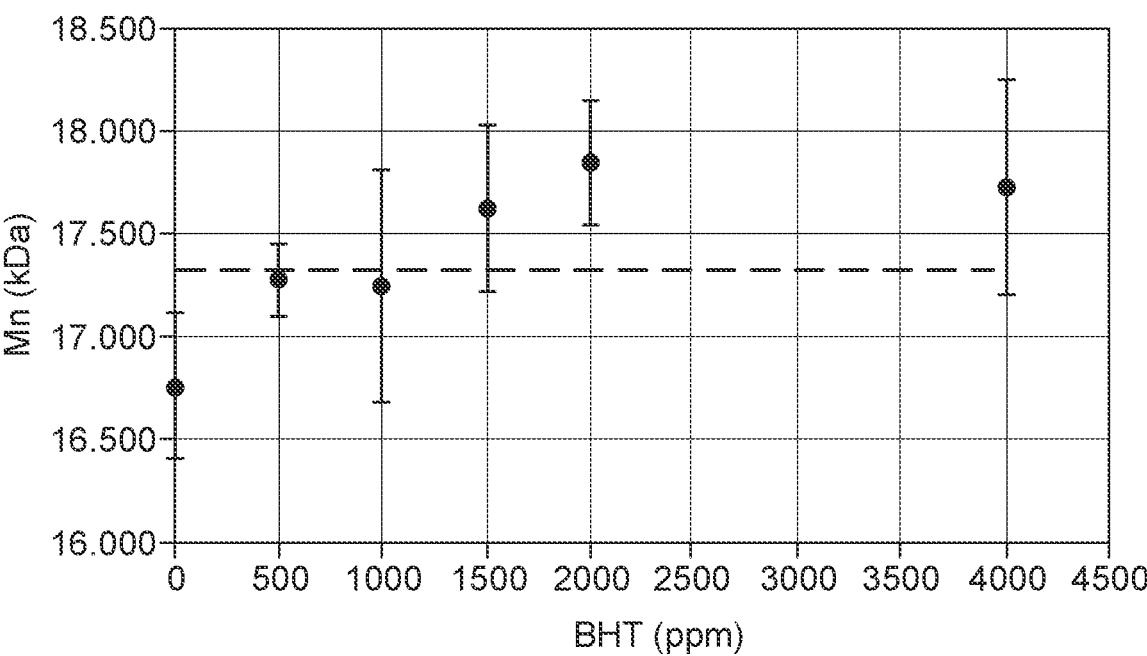
Figure 10B:
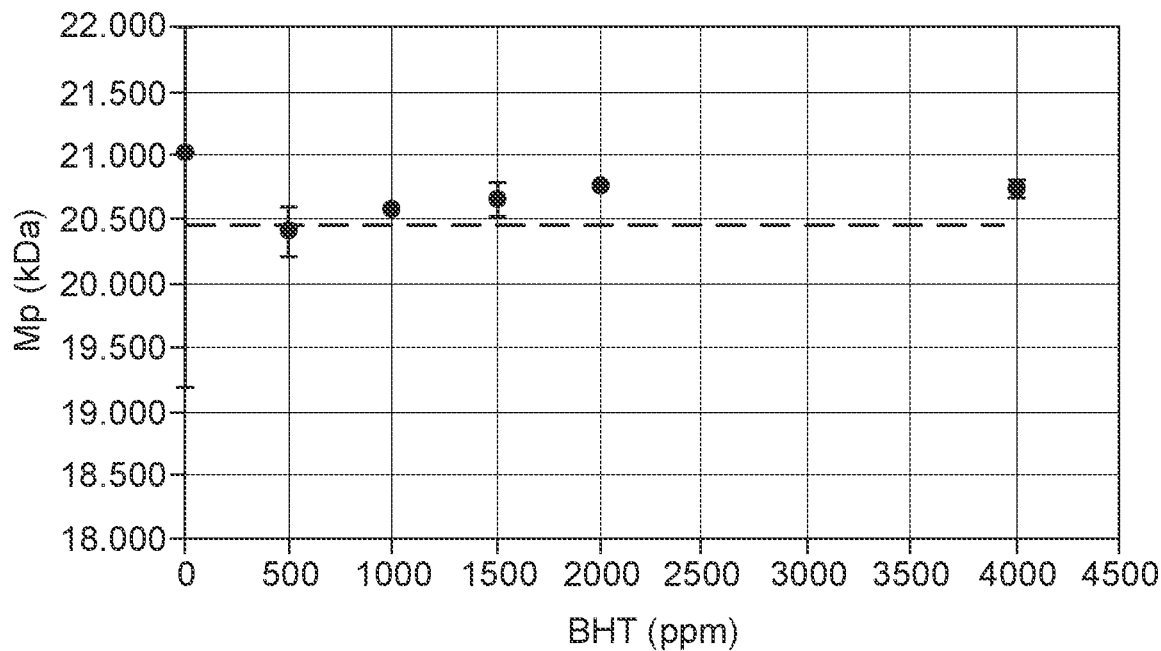
Figure 10C:
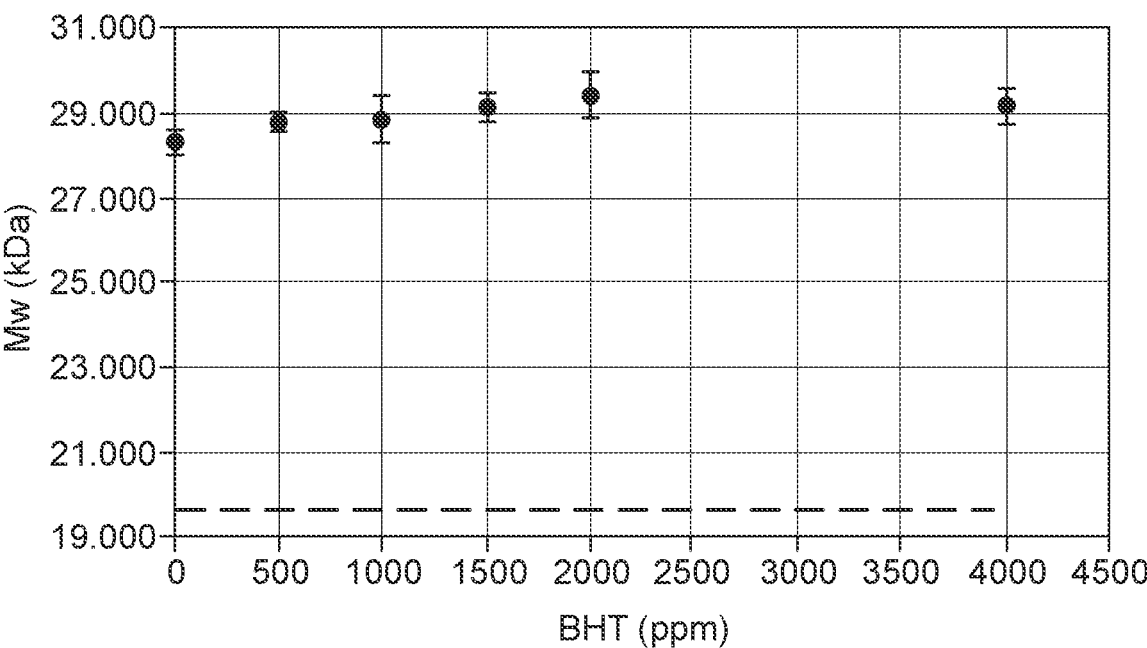
Figure 10D:
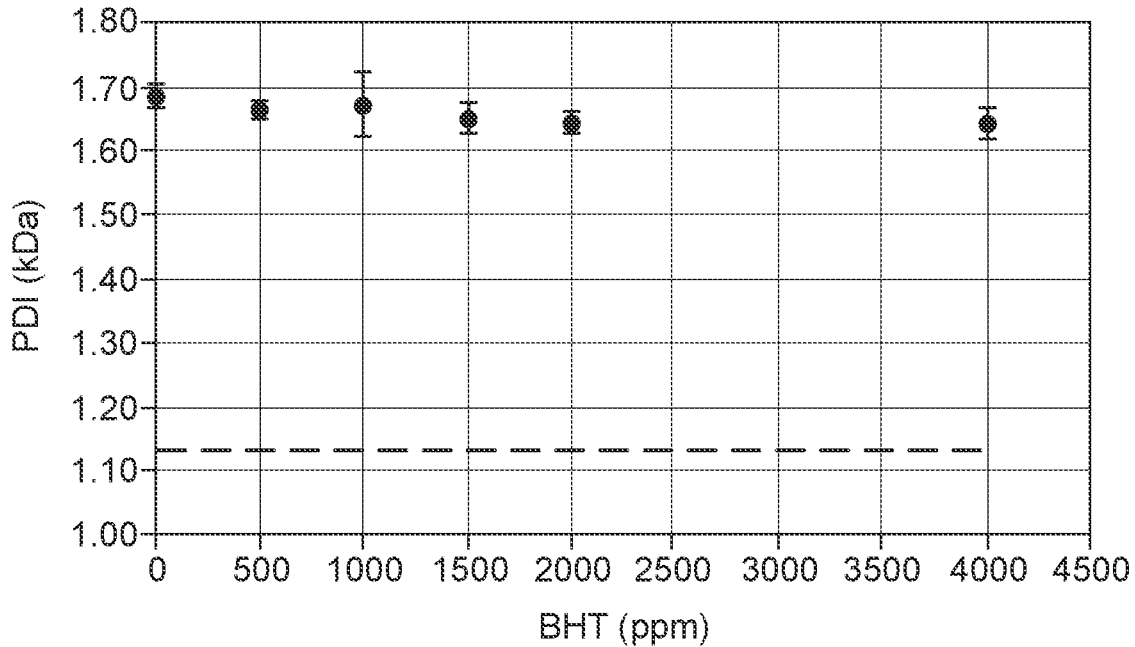

FIGS. 10A-10D are graphs showing evaluation of BHT at varying concentrations for reduction in adverse effects of irradiation on 4-arm PEG-OH with respect to Mn (number average molecular weight) (FIG. 10A), Mp (molecular weight of the highest peak) (FIG. 10B), Mw (weight average molecular weight) (FIG. 10C), and the polydispersity index (PDI) (FIG. 10D).

Figure 11A:
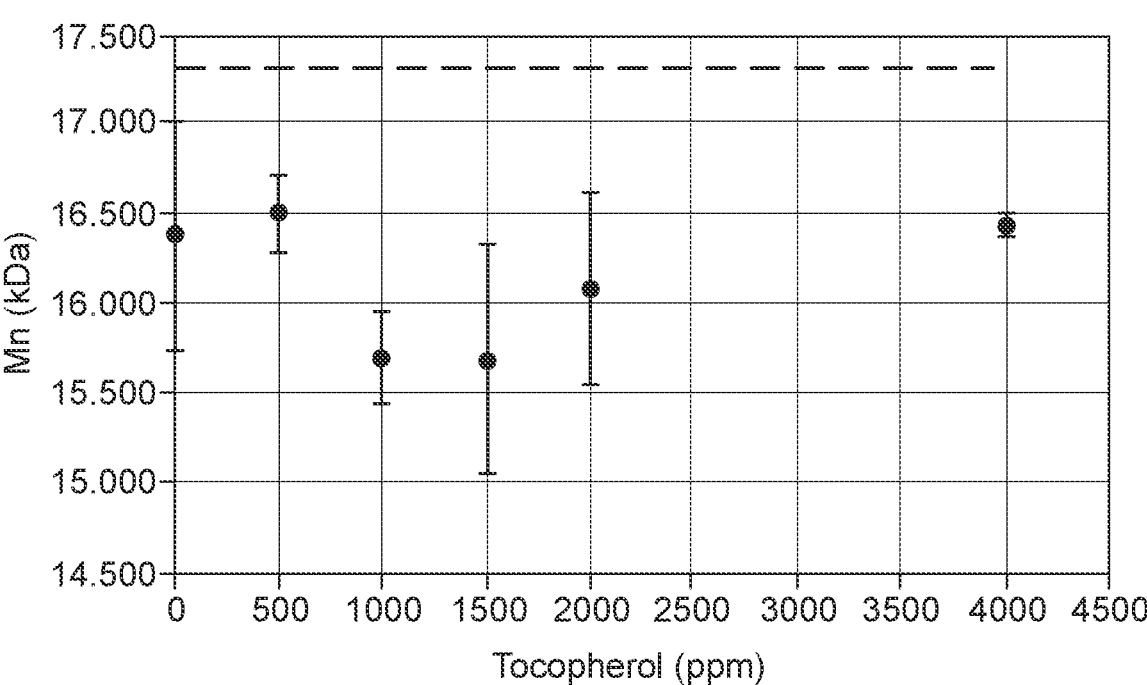
Figure 11B:
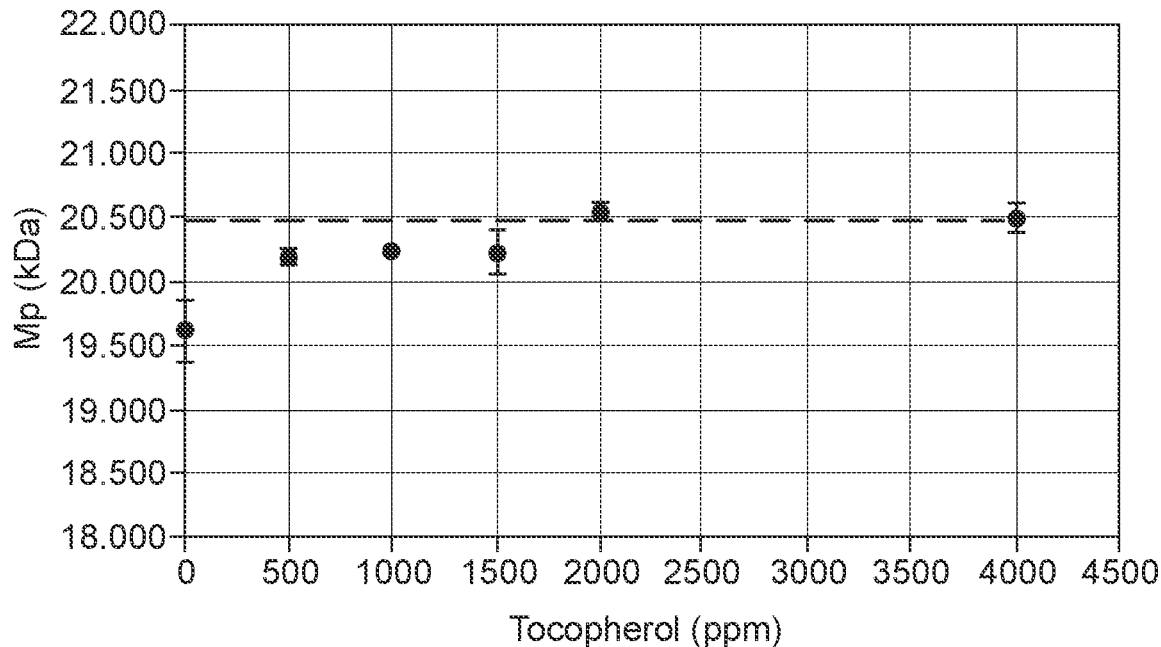
Figure 11C:
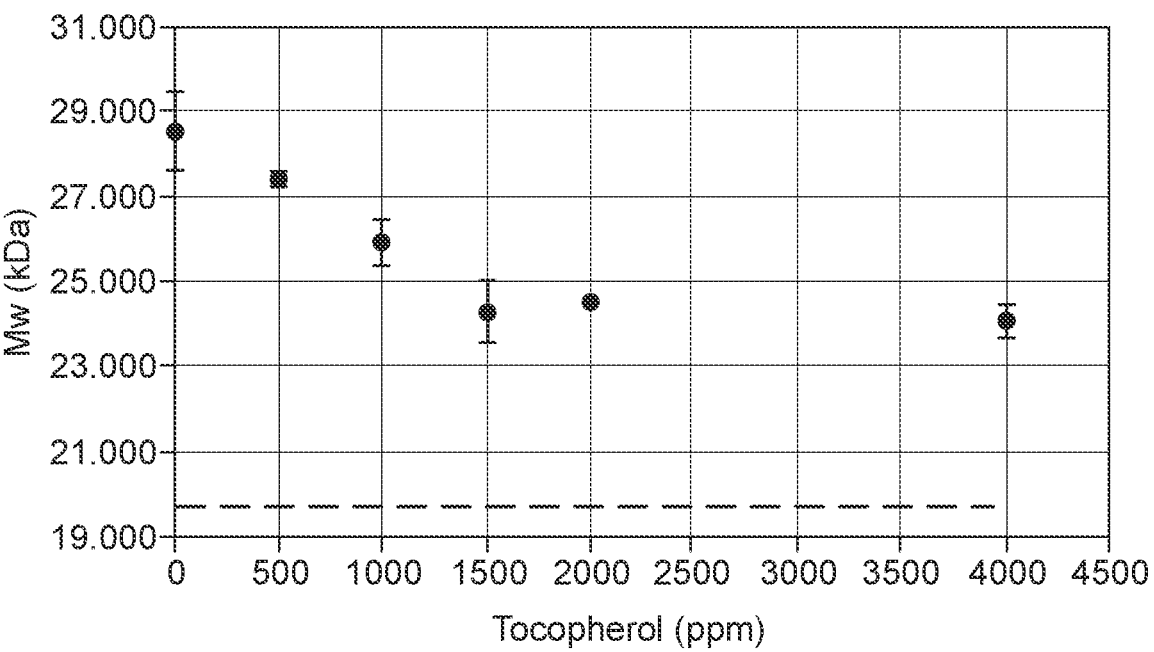
Figure 11D:
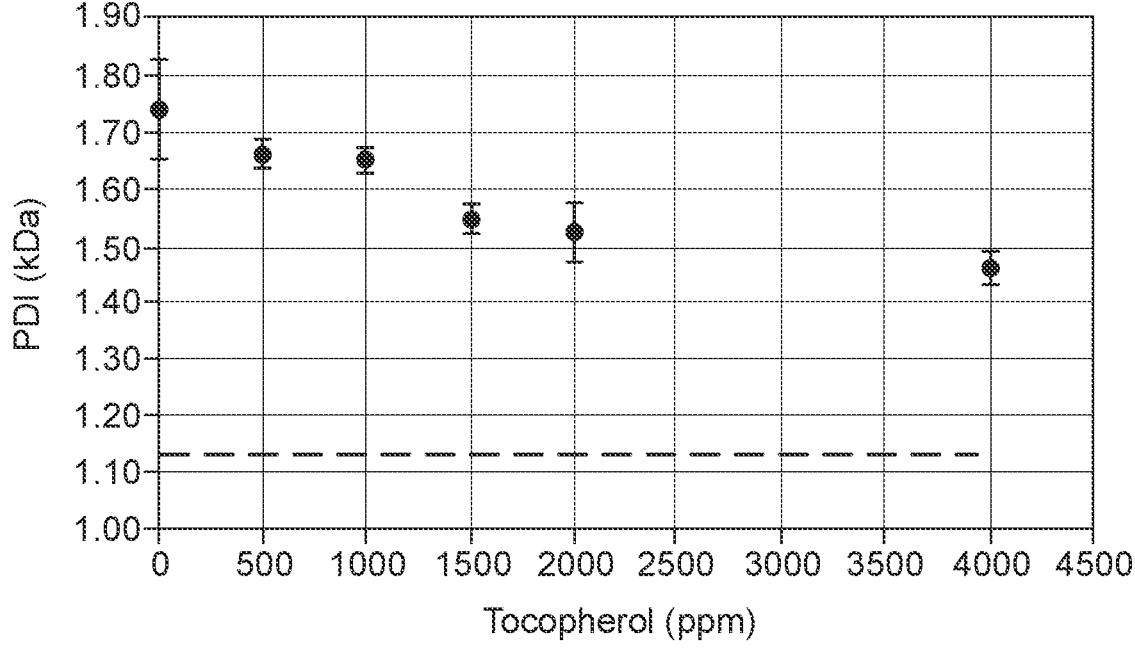

FIGS. 11A-11D are graphs showing evaluation of tocopherol at varying concentrations for reduction in adverse effects of irradiation on 4-arm PEG-OH with respect to Mn (number average molecular weight) (FIG. 11A), Mp (molecular weight of the highest peak) (FIG. 11B), Mw (weight average molecular weight) (FIG. 11C), and the polydispersity index (PDI) (FIG. 11D).

Figure 12A:
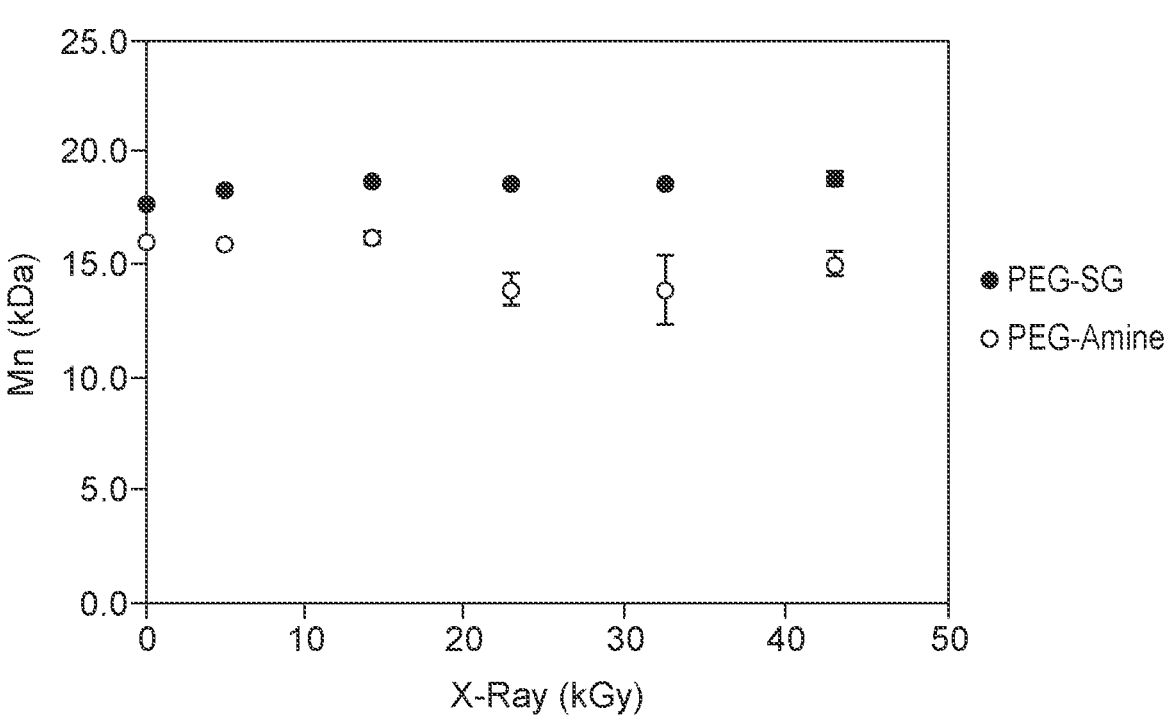
Figure 12B:
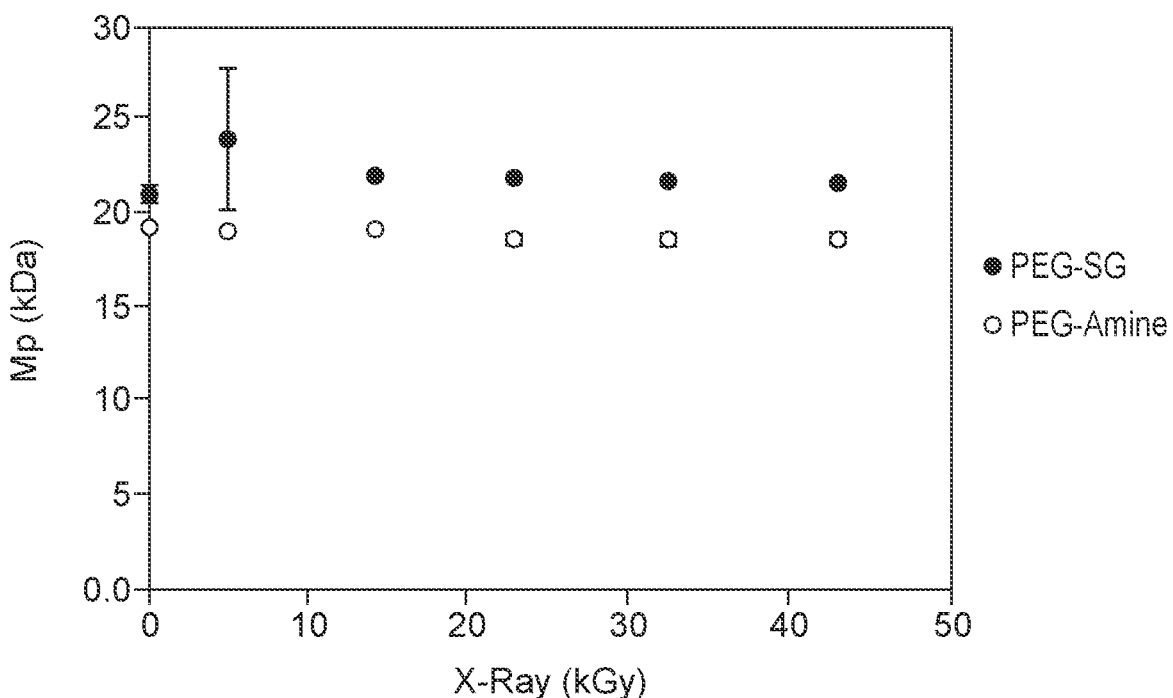
Figure 12C:
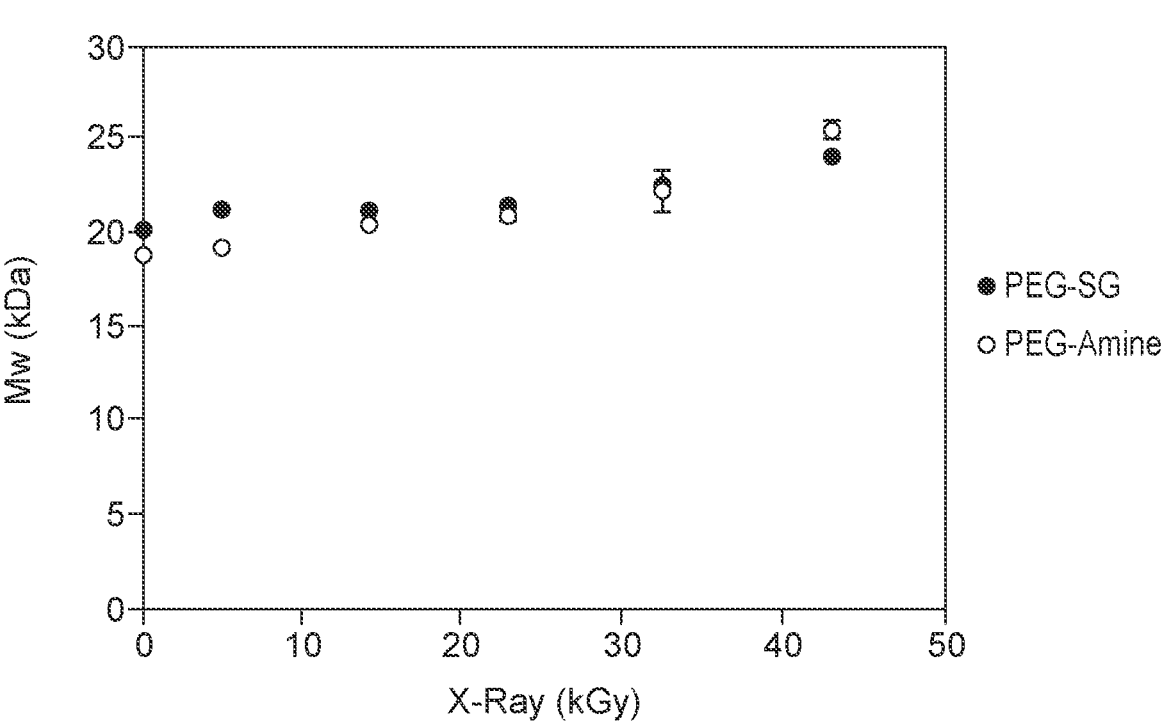
Figure 12D:
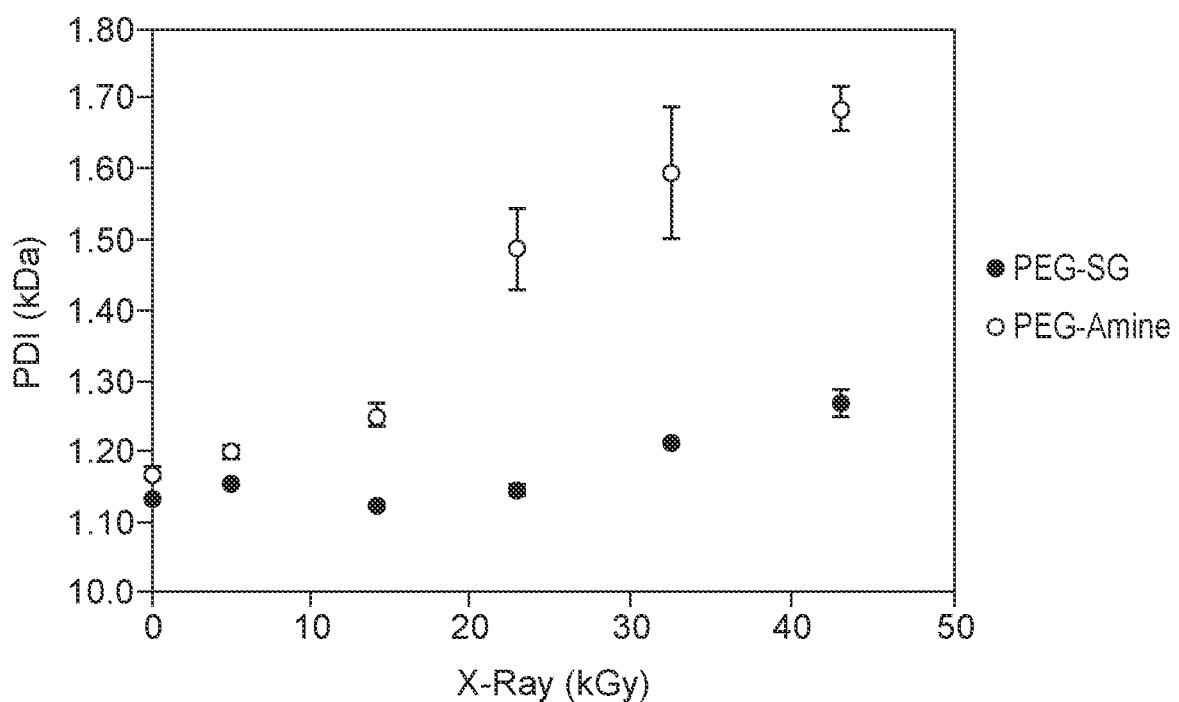

FIGS. 12A-12D are graphs showing evaluation of 2000 ppm (±)-α-tocopherol (tocopherol) on the lung sealant PEGs to reduce the effects of irradiation with respect to Mn (number average molecular weight) (FIG. 12A), Mp (molecular weight of the highest peak) (FIG. 12B), Mw (weight average molecular weight) (FIG. 12C), and polydispersity index (PDI) (FIG. 12D)

Figure 13:
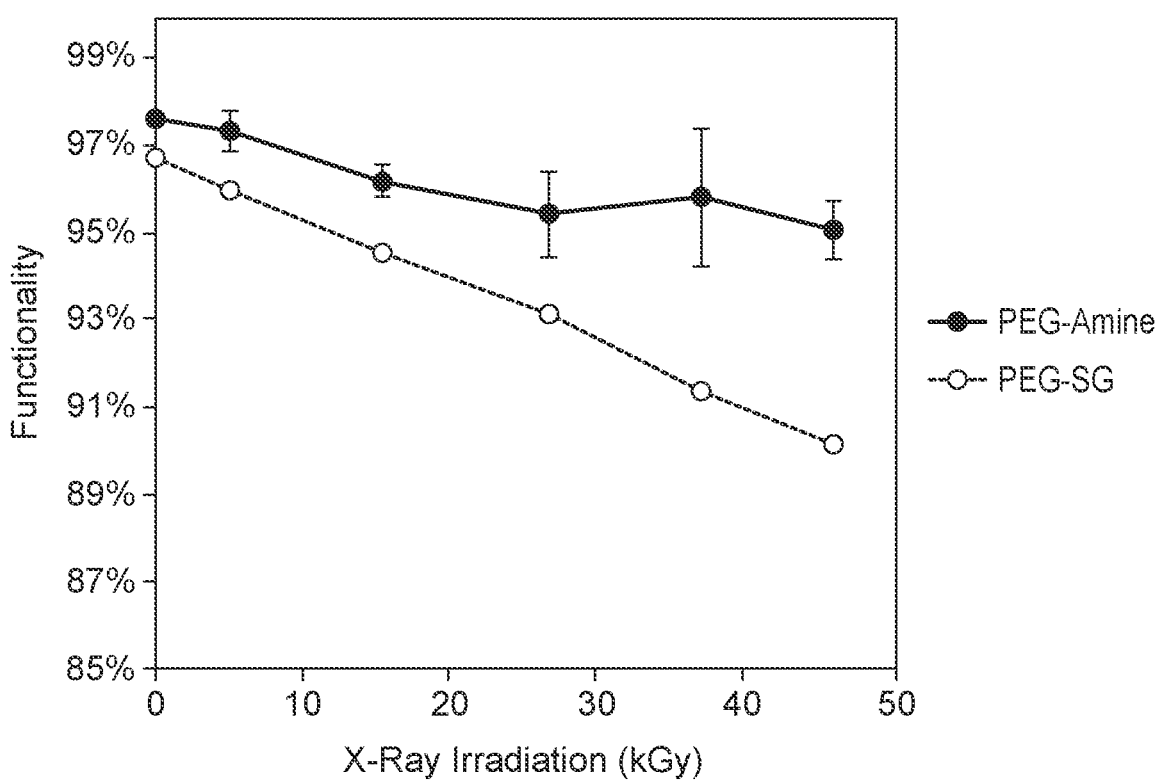

FIG. 13 is a graph showing the dose dependent effect of X-ray irradiation (kGy) on PEG-SG and PEG-Amine functionality wherein 2000 ppm tocopherol was added to each of the PEG-SG and PEG-Amine.

Figure 14:
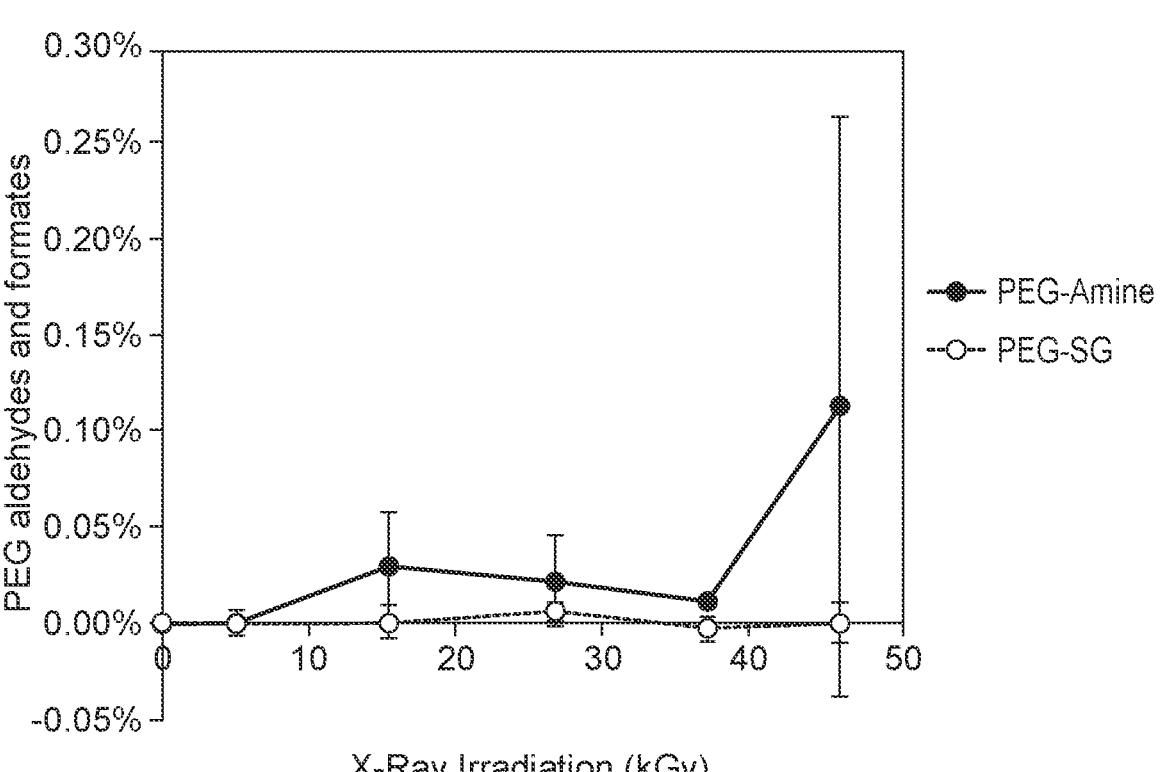

FIG. 14 is a graph showing the effect of varying X-ray irradiation (kGy) doses on aldehyde and formate generation for PEG-Amine and PEG-SG.

Figure 15:
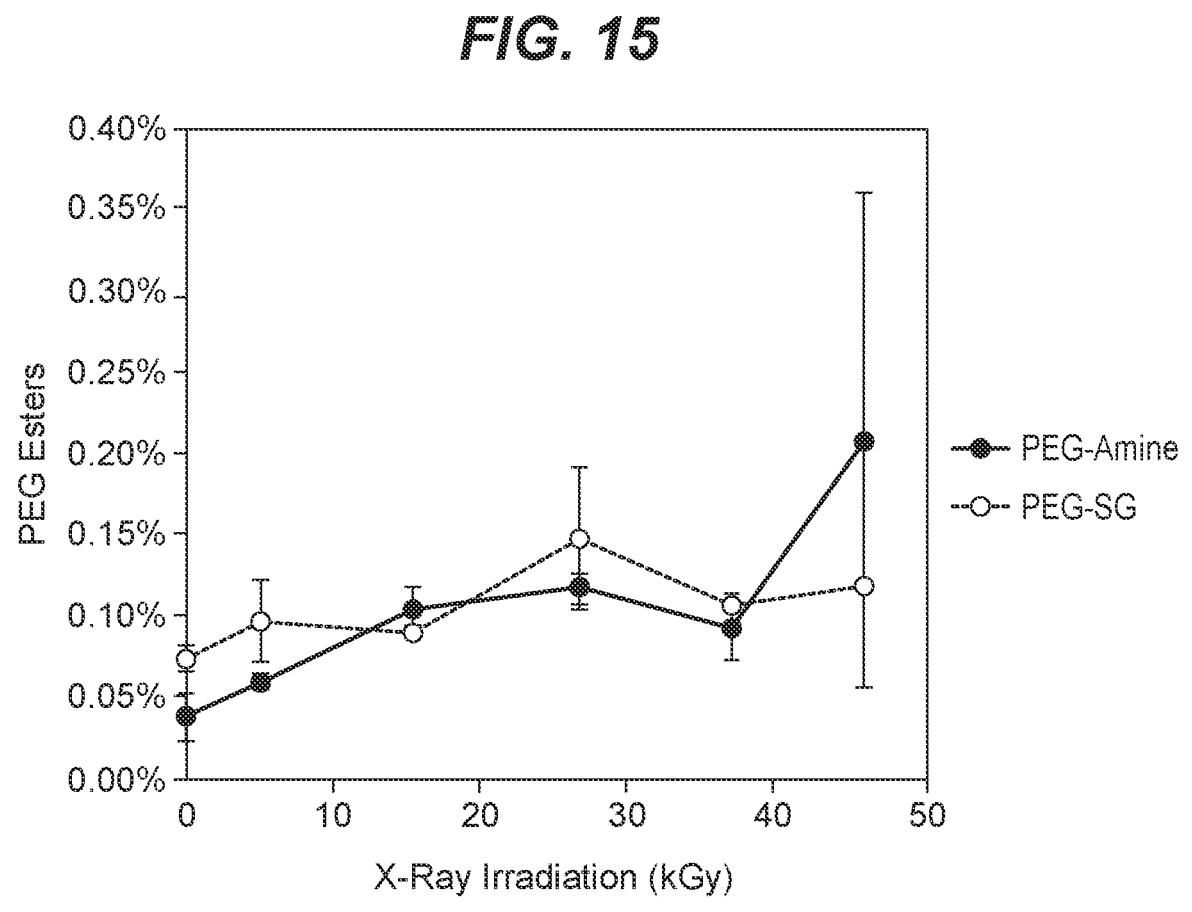

FIG. 15 is a graph showing the effect of varying X-ray irradiation (kGy) doses on generation of PEG esters for PEG-Amine and PEG-SG.

Figure 16:
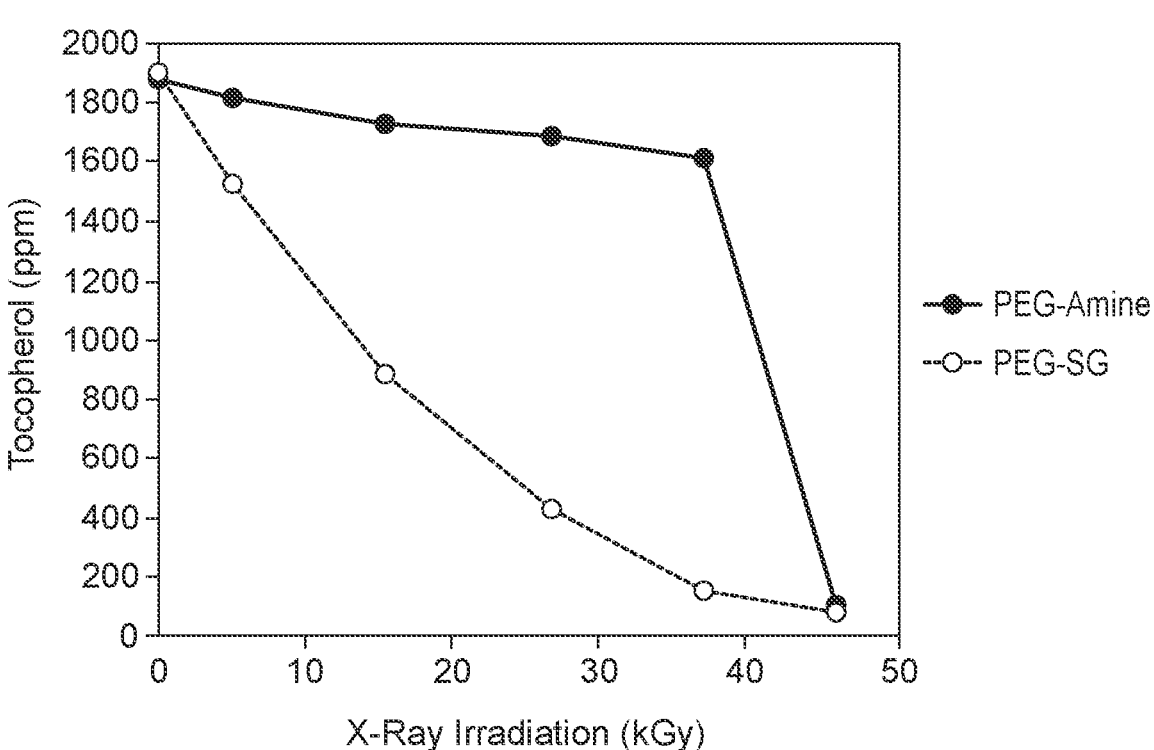

FIG. 16 is a graph showing the loss of the antioxidant tocopherol at varying X-ray irradiation (kGy) doses for PEG-Amine and PEG-SG.

Figure 17:
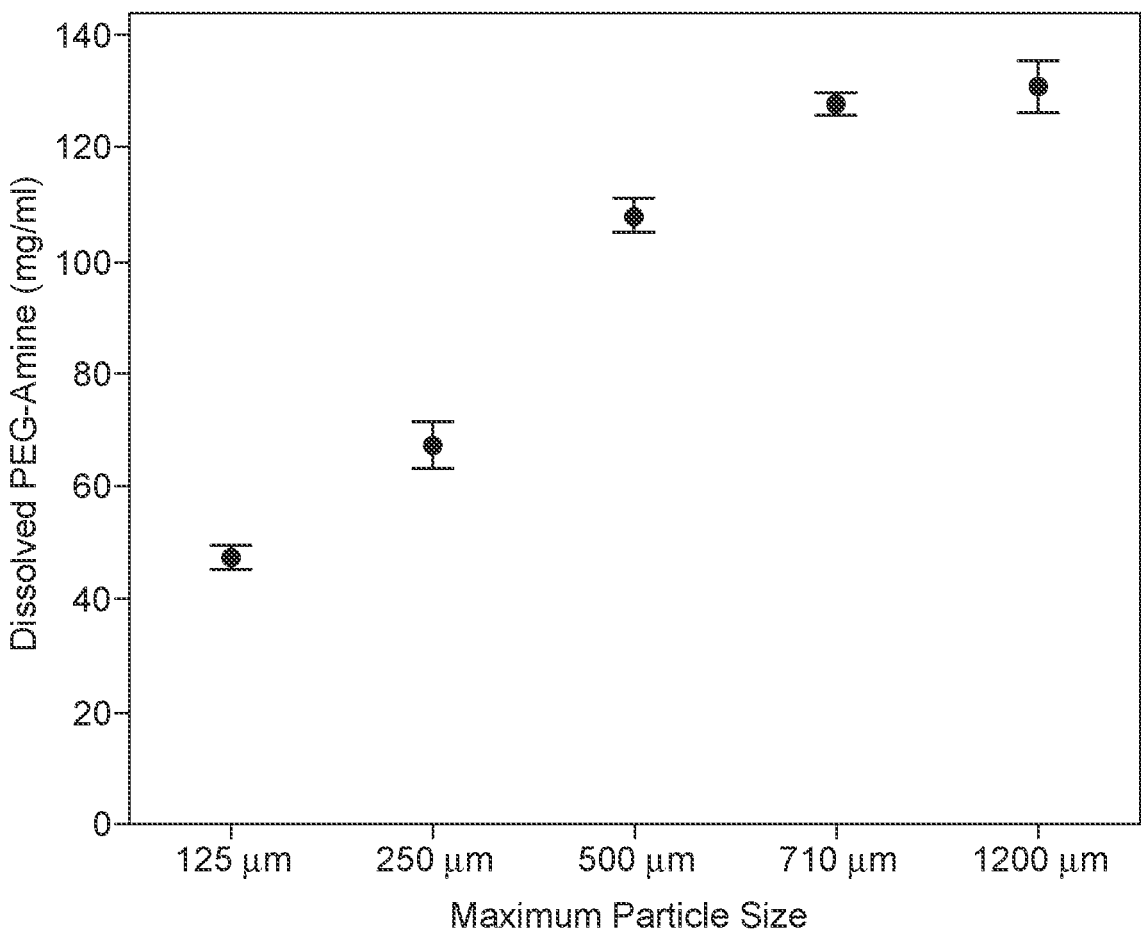

FIG. 17 is a graph showing the extent of dissolution of PEG-Amine samples at varying particle sizes at controlled maximum value.

Figure 18:
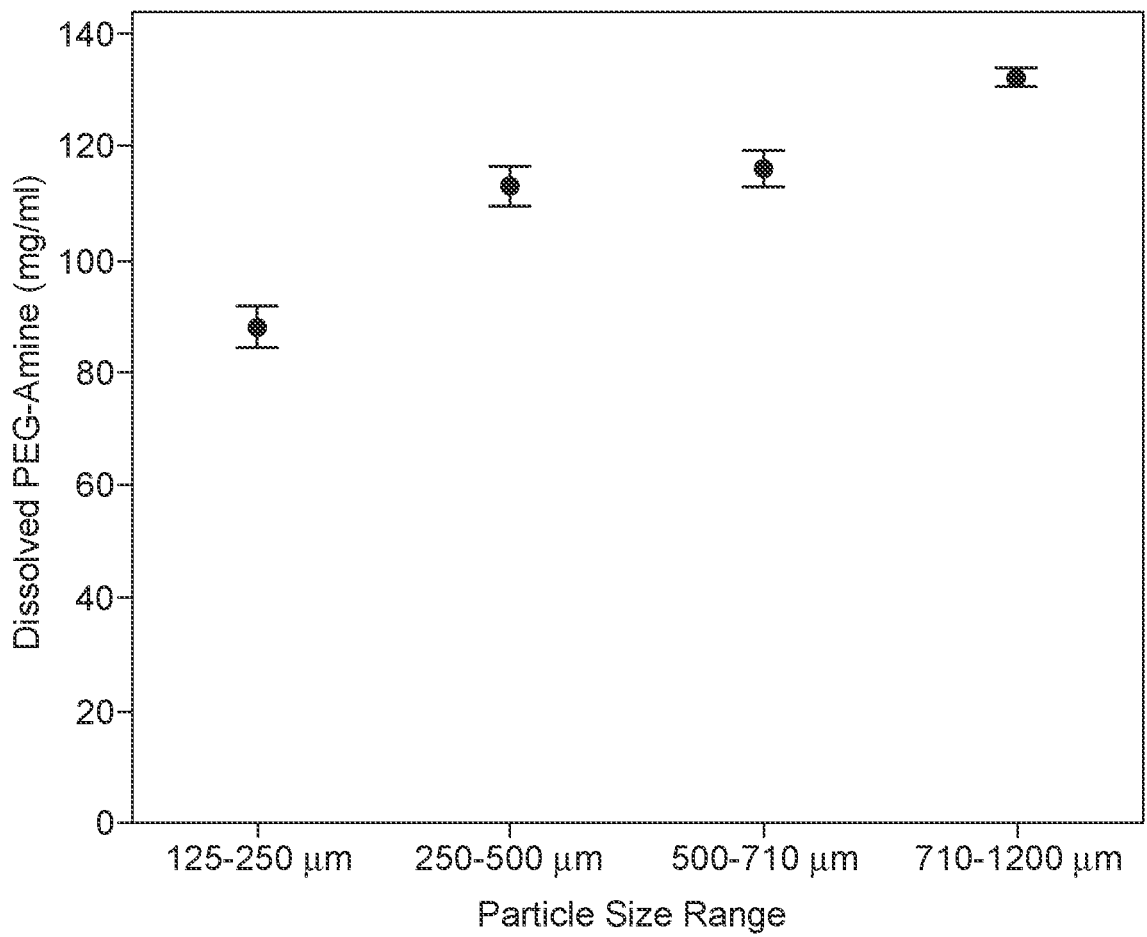

FIG. 18 is a graph showing the extent of dissolution of PEG-Amine samples at varying particle sizes with a controlled minimum and maximum range.

Figure 19:
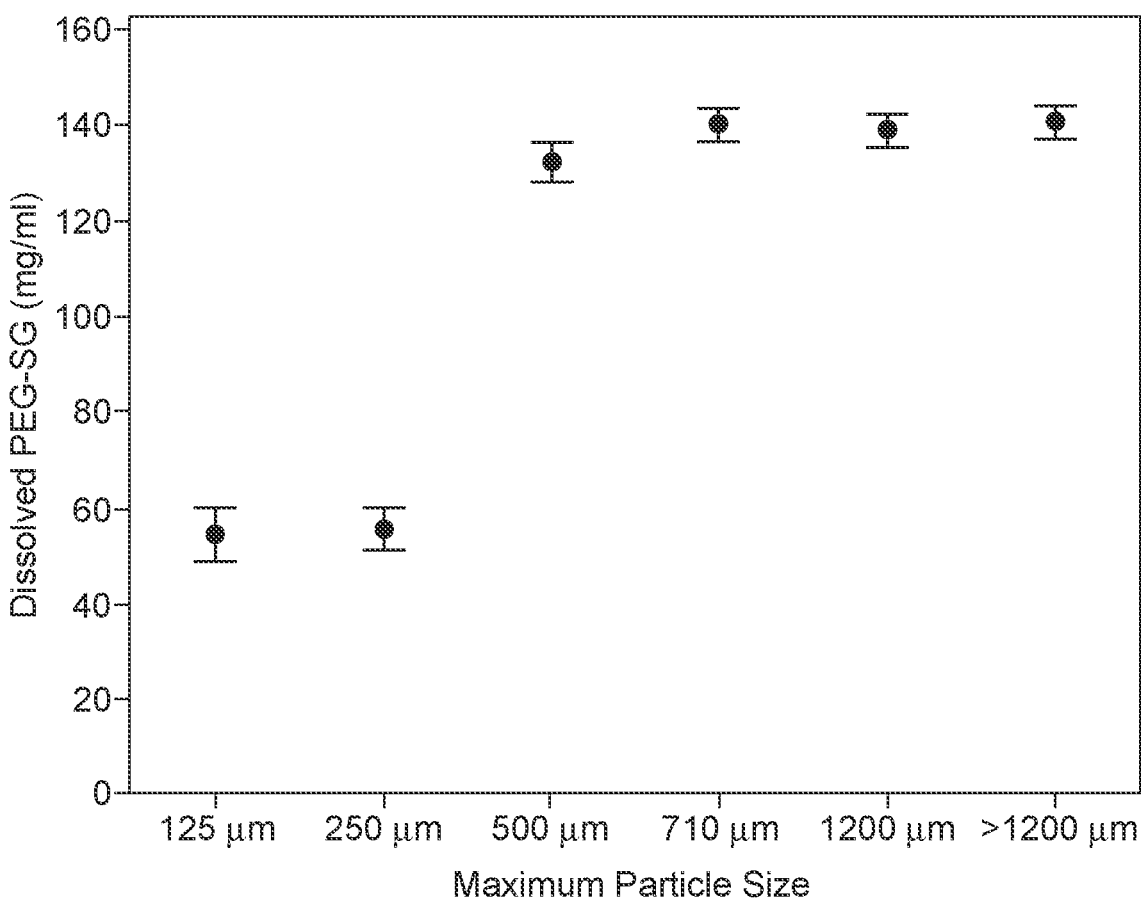

FIG. 19 is a graph showing the extent of dissolution of PEG-SG samples at varying particle sizes at controlled maximum values.

Figure 20:
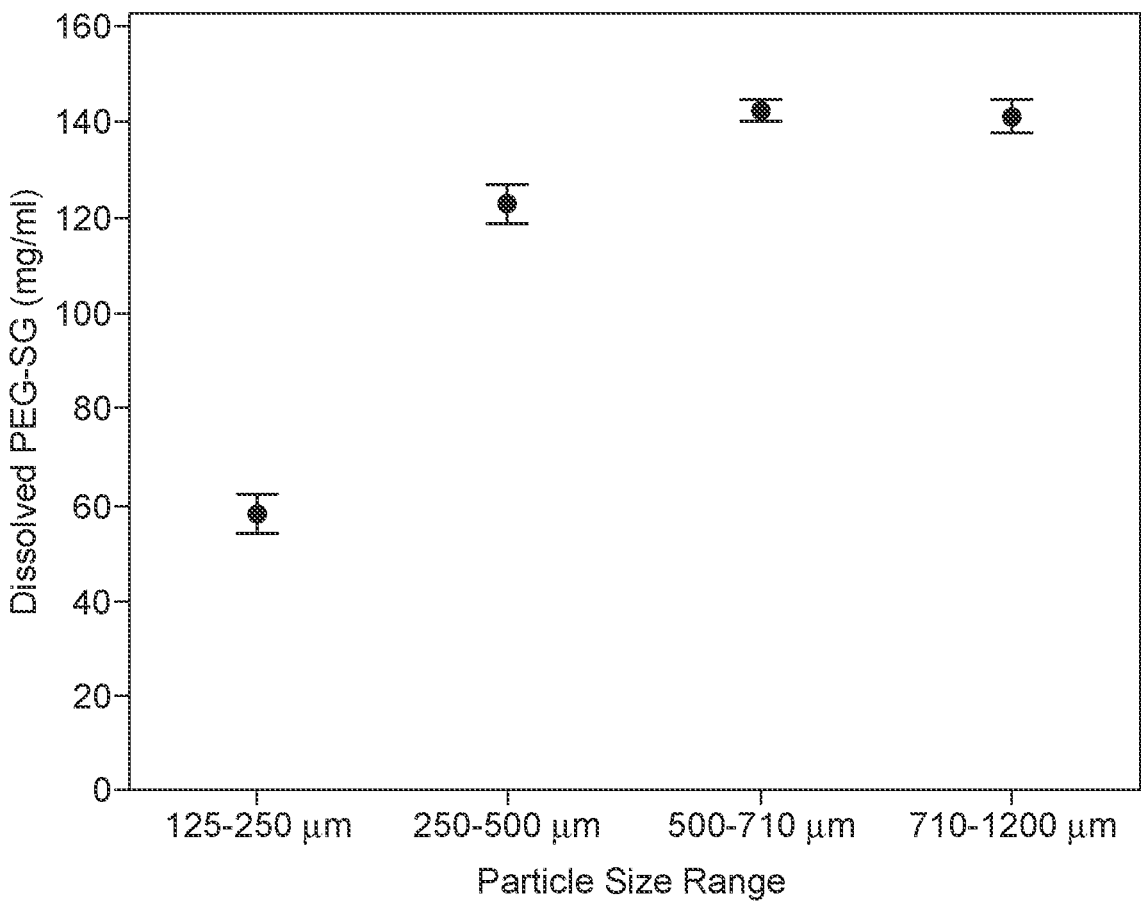

FIG. 20 is a graph showing the extent of dissolution of PEG-SG samples at varying particle sizes with a controlled minimum and maximum range.

Figure 21:
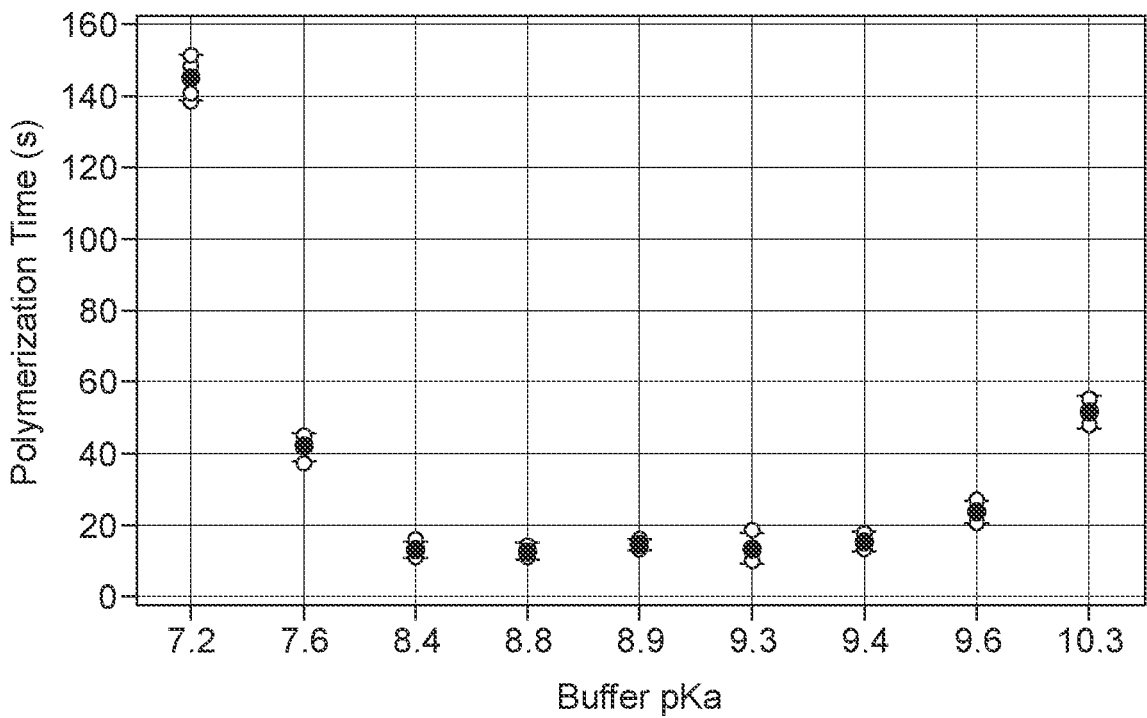

FIG. 21 is a graph showing the effect of buffer pKa on polymerization time of PEG-SG and PEG-Amine.

Figure 22:
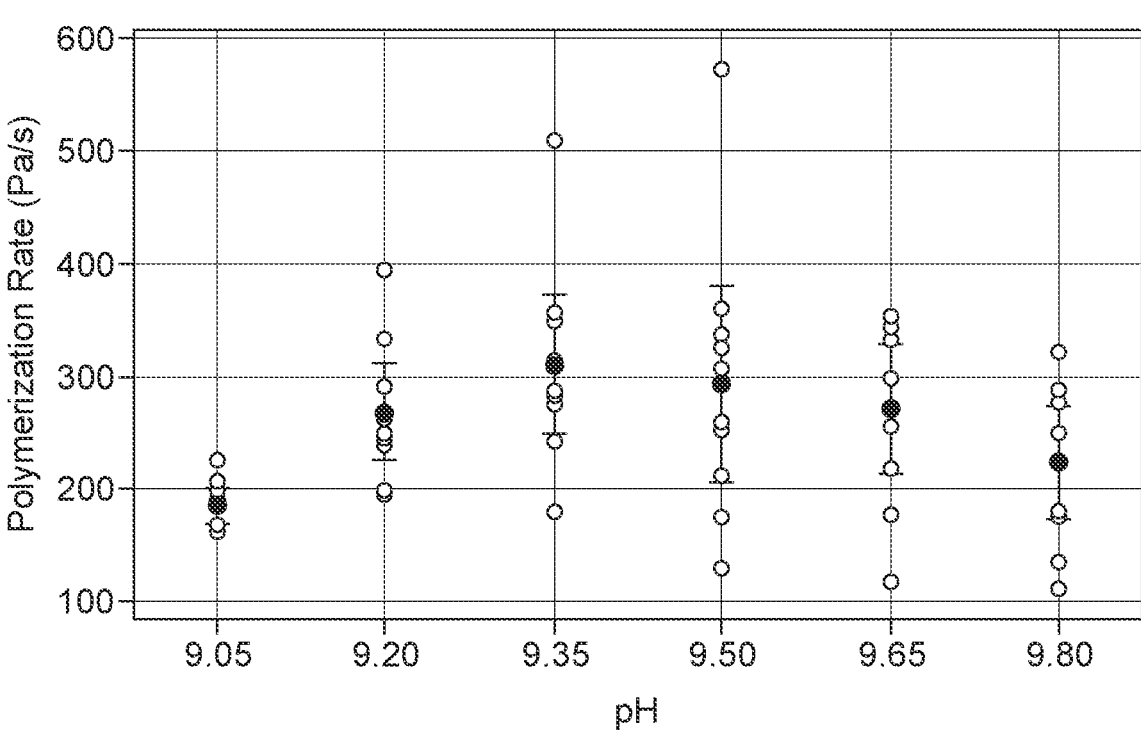

FIG. 22 is a graph showing the effect of varying CHES pH on the polymerization rate of PEG-Amine (HCl salt).

Figure 23:
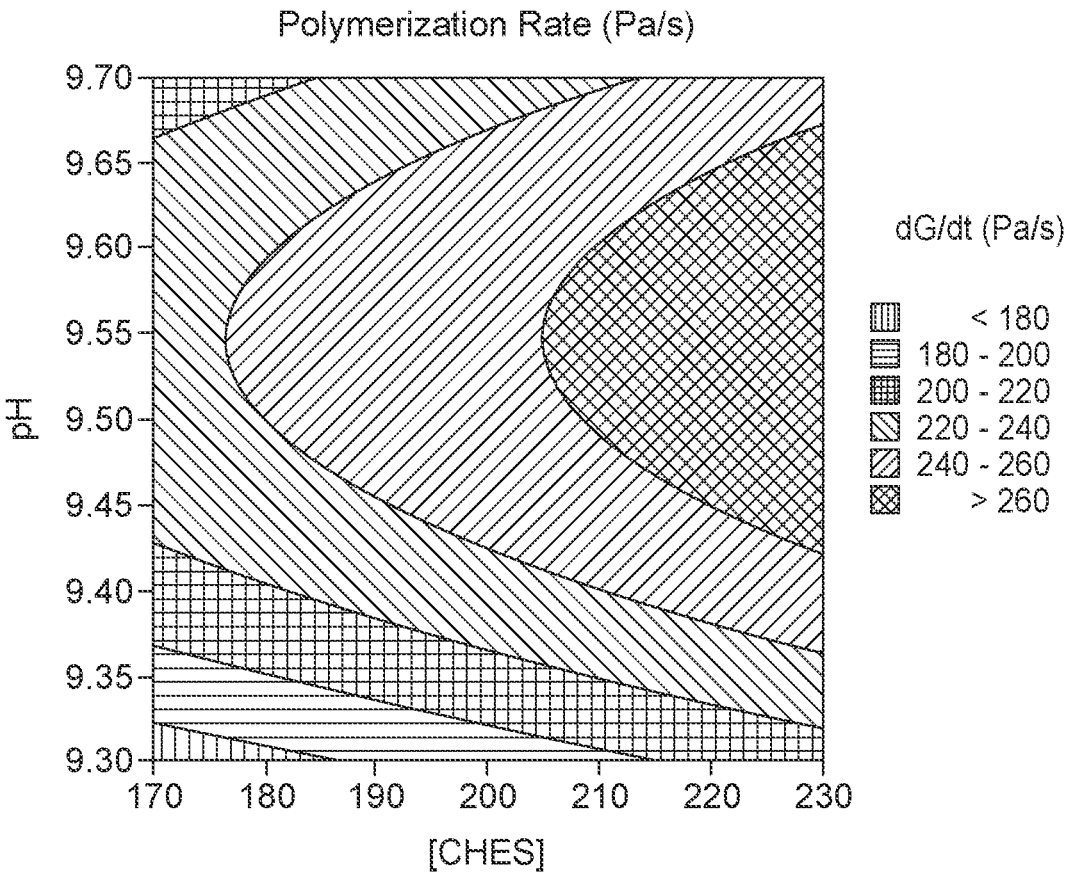

FIG. 23 is a contour plot of the polymerization rate response at varying pH and CHES concentrations.

Figure 24:
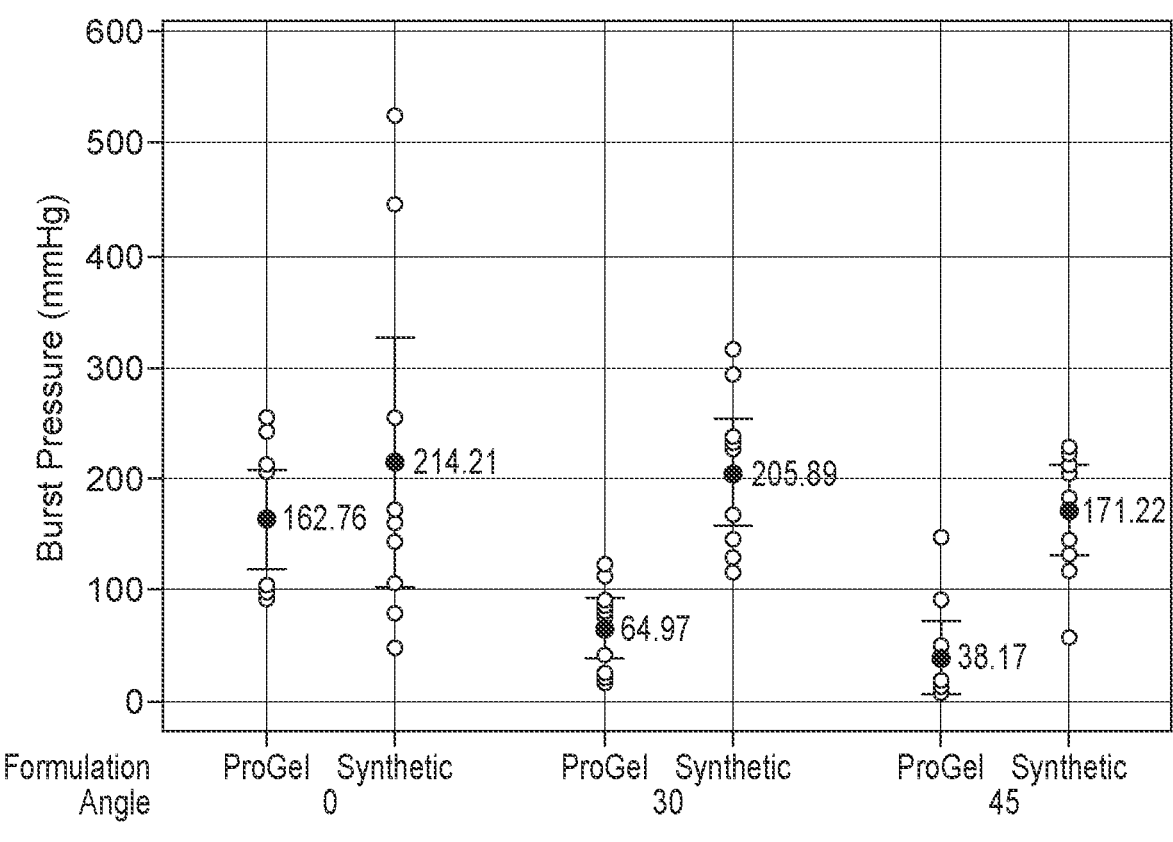

FIG. 24 is a graph showing the results of a burst pressure test performed at various angles to demonstrate how the lung sealants of the invention improved ability to remain in place affects performance compared to Mock PROGEL™ hydrogel.

Figure 25:
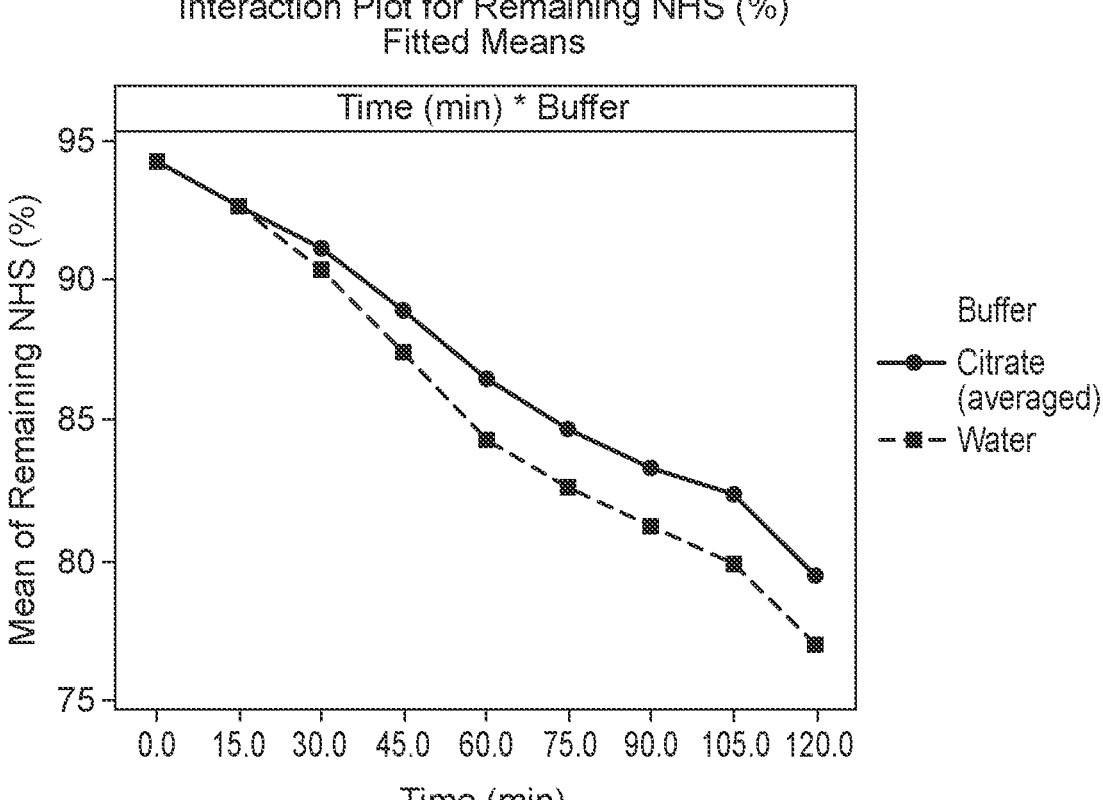

FIG. 25 is an interaction plot showing citrate buffer reduction of PEG-SG hydrolysis.

DETAILED DESCRIPTION

The biodegradable lung sealants of the present invention are applied as a liquid that is rapid setting to remain at the target tissue location and provide an adequate seal. The sealants have improved elasticity, tensile strength, visualization, and working time.

Moreover, the sealants of the present invention surprisingly and unexpectedly have advantageous shear moduli, polymerization times and polymerizations rates for sealing lung tissue. In one aspect, the lung sealants provided herein comprise a combination of equal molecular weight polyethylene glycol (PEG) polymers and an optimal buffer system. PEGs having a molecular weight of about 15 kDa to about 50 kDa are preferred for use in the lung sealants of the invention.

The polymerization kinetics of the lung sealants provided herein can be determined as follows:

(a) Maximum shear modulus, a measure of the stiffness of the sealant;

(b) Polymerization time (k), defined as the time required to achieve 50% of the final mechanics of the sealant; and (c) Polymerization rate defined as the maximal slope of the shear modulus.

Polymerization time (k) analyzes the shear modulus over time normalized to the maximum shear modulus. Polymerization time provides an understanding of cure time (the time required to achieve final mechanics), but also allows for an indirect determination of set time, i.e., the time required for the sealant to stop flowing. Set time cannot be directly quantified as the sealant sets within a few seconds.

Polymerization rate provides a measurement of the rate at which the sealant increases in shear modulus over time. The polymerization rate is sensitive to both polymerization time and final hydrogel mechanics.

The efficacy of the sealant, or the sealant's ability to provide a strong seal, is dictated by the sealant's mechanics. The sealant mechanics are measured via cohesive tensile testing and shear modulus.

PEGs suitable for use in the lung sealants of the present invention are multi-arm PEGs, such as 2, 3, 4, 6 or 8 multi-arm PEGs. In some preferred embodiments, the PEGs are 4-arm PEGs. In some aspects, the multi-arm PEG is a multi-arm PEG derivative. In some embodiments, the multi-arm PEG derivative is a multi-arm PEG-Amine hydrochloride (HCl) salt. For example, multi-arm PEGs are commercially available from JenKem Technology (Plano, Texas) or NOF Corporation (Tokyo, Japan). In some embodiments, the multi-arm PEG has a molecular weight of about 15 kDa to about 50 kDa, and most preferably about 20 kDa. In some embodiments, the lung sealants provided herein comprise multi-arm PEGs with reactive functional groups at each termini of the arms, such as N-hydroxysuccinimide (NHS) ester groups which can form stable conjugates, i.e, amide bonds, with PEG-Amines. Examples of suitable PEGs for use in the sealants provided herein are 4-arm PEG-succinimidyl glutarate (SG), 4-arm PEG-succinimidyl valerate, 4-arm PEG-succinimidyl carbonate, 4-arm PEG-succinimidyl succinate, 4-arm PEG-succinimidyl butanoate, 4-arm PEG-succinimidyl succinamide, 4-arm PEG-succinimidyl propionate, 4-arm PEG-sulfosuccinimidylglutarate, 4-arm PEG-sulfosuccinimidylvalerate, 4-arm PEG-sulfosuccinimidylcarbonate, 4-arm PEG-succinimidlyl carboxymethyl ester, 4-arm PEG-sulfosuccinimidylsuccinate, 4-arm PEG-sulfosuccinimidylbutanoate, 4-arm PEG-sulfosuccinimidylsuccinamide, 4-arm PEG-sulfosuccinimidylpropionate, 4-arm PEG-Amine, 4-arm PEG-isocyanate, 4-arm PEG-imidoester, and 4-arm PEG-maleimide.

In another aspect, the sealants provided herein can include thiols reactive with PEG-NHS esters and PEG-maleimides.

In some embodiments, the lung sealants include PEGs at a total final concentration in the sealant of from about 39 mg/mL to about 87 mg/mL. In a preferred embodiment the total concentration of each of the PEGs is about 67 mg/mL. Examples of preferred PEGs are 4-arm PEG-succinimidyl glutarate, M.W. 20 kDa (4-arm-PEG-SG-20K) (67 mg/mL) available from JenKem Technology or NOF Corporation, and 4-arm PEG-Amine, M.W. 20 kDa (4-arm-PEG-NH2-20K) (67 mg/mL) available from JenKem Technology or NOF Corporation. In one aspect, the PEG-SG and PEG-Amine final concentrations in the sealant applied to a tissue are each about 39 mg/mL to about 87 mg/mL, preferably about 52 mg/mL to about 77 mg/mL and, more preferably, about 67 mg/mL.

The particle size distribution of off-the-shelf PEG results in maximum dissolution using the methods provided herein for preparing the biodegradable lung sealants of the present invention. However, particle size has a significant effect on the dissolution rate of the PEGs. Unexpectedly, larger particle sizes result in faster dissolution by decreasing the tendency of the PEGs to aggregate and adhere to the glass vial walls.

For PEG-Amine, a maximum particle size of at least 710 μm is preferred. For PEG-SG (as it is dissolved in a lower concentration buffer), a maximum particle size of at least 500 μm is most preferable. Lower maximum particle sizes will dissolve, but require longer preparation times.

In another aspect, suitable buffers for use in preparing the lung sealants of the present invention are alkaline buffers, such as, N-cyclohexyl-2-aminoethanesulfonic acid (CHES) buffer, 2-Amino-2-methyl-1,3-propanediol, N-tris(Hydroxymethyl)methyl-4-aminobutanesulfonic acid, N-(1,1-dimethyl-2-hydroxyethyl)-3-amino-2-hydroxypropane-sulfonic acid, 3-(Cyclohexylamino)-2-hydroxy-1-propanesulfonic acid, pyridoxine buffer, and mildly acidic buffers, such as citrate buffer. Preferably, the mildly acid buffer has a pH of about 4 to about 6 or up to 7.

Carbonate buffers are not preferred due to insufficient buffer capacity at pH of 9 leading to increased runniness. Although runniness can be decreased at higher pH, undesirable hydrolysis and tissue reaction can occur.

A higher molecular weight PEG results in a lung sealant having a higher tensile extension at failure. However, larger molecular weight PEGs can demonstrate reduced renal clearance and undesirable longer half-life. In a preferred embodiment, 20 kDa molecular weight PEG provides a desirable balance between hydrogel mechanics and excretion/clearance time. In one aspect, the molecular weights of the two PEGs are similar or equal. In a preferred aspect, the PEGs are PEG-SG and PEG-Amine each having a molecular weight of 20 kDa.

Figure 5:
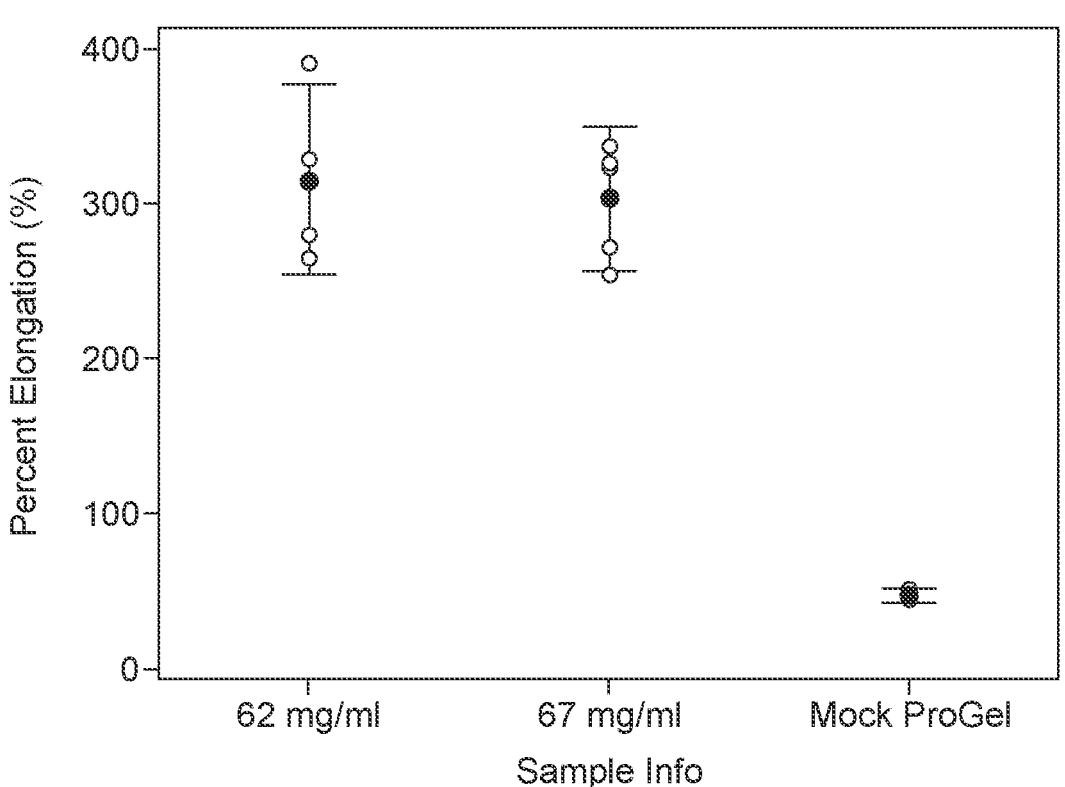
FIG. 5 is a graph showing elongation at failure of two PEG candidates of the invention (Candidate #1: 62 mg/mL PEG-SG and 62 mg/mL PEG-Amine, and Candidate #2: 67 mg/mL PEG-SG and 67 mg/mL PEG-Amine), and Mock PROGEL™ hydrogel (65 mg/mL PEG-succinimidyl succinate, 150 mg/mL Human Serum Albumin, 50 mM carbonate (pH=9.0)). The elongation at failure of the two PEG candidates of the invention was 7.2× greater than Mock PROGEL™ hydrogel.
Figure 6:
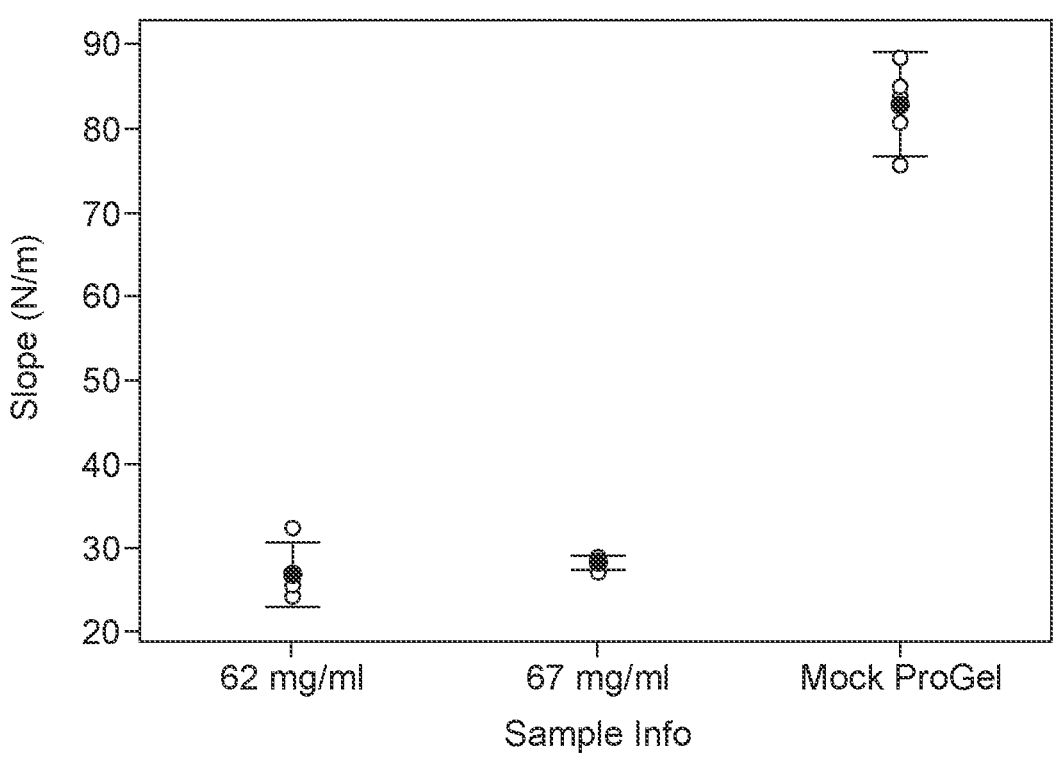
FIG. 6 is a graph showing stiffness of two PEG candidates Candidate #1: 62 mg/mL PEG-SG and 62 mg/mL PEG-Amine, and Candidate #2: 67 mg/mL PEG-SG and 67 mg/mL PEG-Amine) of the invention, and Mock PROGEL™ hydrogel (65 mg/mL PEG-succinimidyl succinate.

The stiffness of the lung sealants provided herein is low relative to currently marketed lung sealants. Surprisingly and unexpectedly, the lung sealants herein exhibit greater strength, elasticity, and compliance than currently marketed products. For example, the elongation at failure of the lung sealants of the present invention is about 7× greater than a Mock PROGEL™ hydrogel formulation (FIG. 5), and the stiffness is about 2.9× lower than a Mock PROGEL™ hydrogel formulation (FIG. 6).

In some aspects, the radioprotector, such as tocopherol, mitigates changes in molecular weight (MW) of the PEGs. Irradiation of the PEGs is preferably performed under a low oxygen environment.

The PEG-Amine is preferably in the protonated form to prevent large irradiation induced decreases in functionality.

In some embodiments of the present invention, the lung sealant includes a colorant. In some aspects, a colorant is included in one or both of the dry PEG powders. In another aspect, the colorant is compounded into the dry PEG-SG powder. Examples of colorants for use in the lung sealants of the invention are FD&C Blue #1, FD&C Blue #2, FD&C Green #3, FD&C Yellow #6, and combinations thereof. In a preferred embodiment, about 1000 ppm to about 1600 ppm of the colorant FD&C Blue #1 is compounded into the dry PEG-SG powder. Preferably, the final concentration of the FD&C Blue #1 in the lung sealants of the invention is about 50 ug/mL to about 100 ug/mL.

In one embodiment, a kit is provided comprising two dry PEG powders and two buffers. In a preferred embodiment the kit includes dry 4-arm PEG-Amine powder and dry 4-arm PEG-SG powder, CHES buffer, and citrate buffer.

The pH of the PEG-Amine solution after dissolution is preferably about 9.0 to about 10.5, more preferably about 9.20 to about 9.80, and most preferably about pH 9.35.

The lung sealants of the present invention can be used to prevent prolonged air leak (PAL), after lung volume reduction (LVR), biological lung volume reduction (Bio-LVR), surgical lung volume resection (for example, lung volume resection for treating emphysema), bullectomy, thoracotomy, sternotomy and thoracic surgery.

Additional details with regard to the inventive lung sealants are provided in the following non-limiting examples.

EXAMPLES

Example 1

Effect of molecular weight of PEG polymers on hydrogel mechanics.

To test the tensile strength, elongation at failure, and elastic modulus, a study was performed to understand the effect of molecular weight of PEG-Amine and PEG-SG on the hydrogel mechanics at a constant molarity of each PEG. The PEG-Amine molecular weight was varied from 5 kDa to 20 kDa, and PEG-SG molecular weight was varied from 10 kDa to 20 kDa. A 50 mM carbonate buffer system was employed for all conditions.

Figure 1:
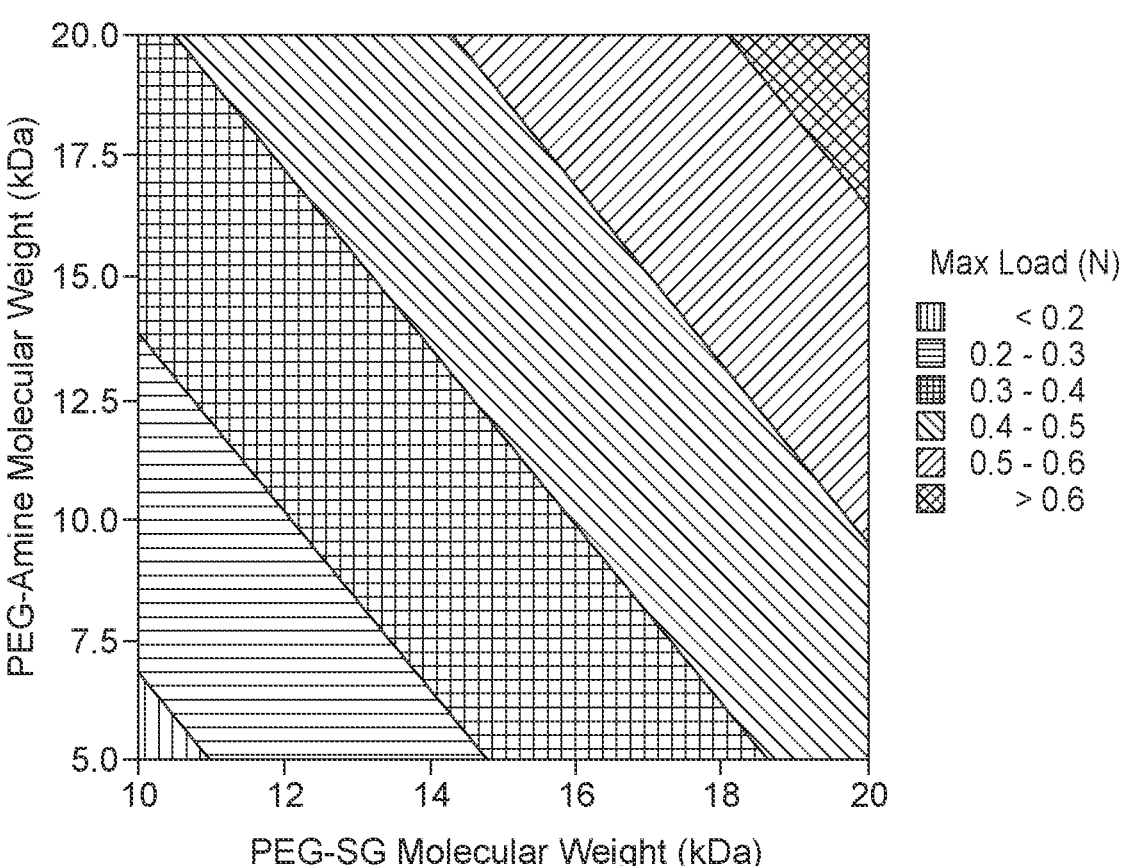
FIG. 1 is a graph showing the effect of varying molecular weights of the PEG-SG and PEG-Amine on the maximum load at failure of the lung sealants.

As shown in the graph in FIG. 1, the maximum load at failure of the sealant formulations tested increased with increasing molecular weight of each PEG and increased most dramatically when both PEG molecular weights were equivalent.

Figure 2:
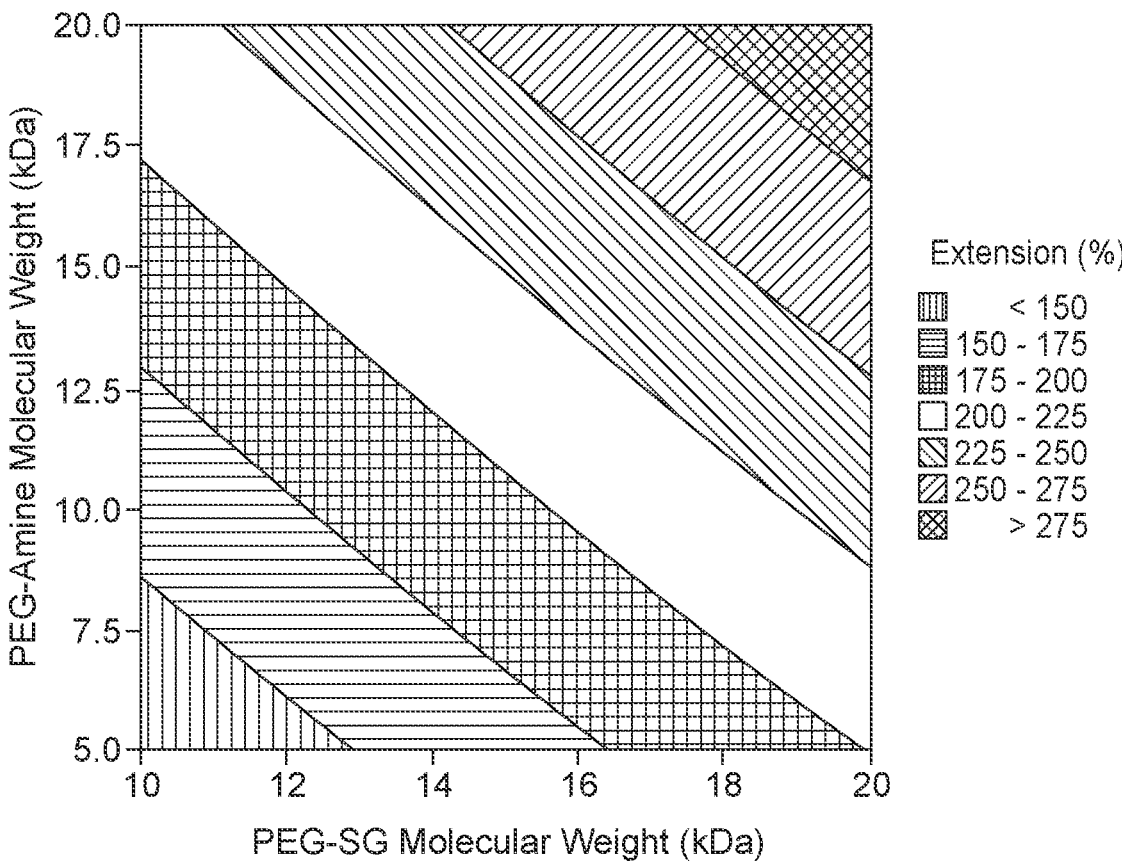
FIG. 2 is a graph showing the effect of varying molecular weights of the PEG-SG and PEG-Amine on the tensile extension at failure of the lung sealants.

Interestingly, as shown in FIG. 2, the tensile extension at failure also increased with increasing the molecular weight of each PEG. However, PEGs having a molecular weight greater than about 50 kDa exhibit reduced renal clearance. A preferred balance between hydrogel mechanics and clearance time was found when each PEG has a molecular weight of 20 kDa.

Example 2

Effect of PEG Concentration on Shear Modulus, Polymerization Time, and Polymerization Rate A study was performed to characterize a range of PEG-SG (20 kDa) and PEG-Amine (20 kDa) concentrations with a 100 mM CHES (pH=9.35), 3.75 mM citrate (pH=5.0) buffer system. The PEG-SG and PEG-Amine were tested by increasing concentrations in equal ratio from 40 mg/mL to 100 mg/mL.

The polymerization kinetics of the sealant were tested via an oscillatory rheometric time sweep at 1 Hz, 150 Pa for 300 seconds. The shear modulus over time was fit to the Hill Equation to provide three outputs:

(1) Maximum Shear modulus, a measure of the stiffness of the formulation;

(2) Polymerization time (k), defined as the time to 50% of final mechanics; and (3) Polymerization rate, defined as the maximal slope of the shear modulus.

In order to analyze the linear effects of such a bulk polymerization system, the study was designed with total polymer content and the ratio of the two reagents as the factors in a central composite design.

$$\text{Total Polymer Content } (PC) = [PEG-SG] + [PEG-Amine]$$

$$\text{Ratio } (r) = \frac{[PEG-SG]}{[PEG-Amine]}$$

Figure 3:
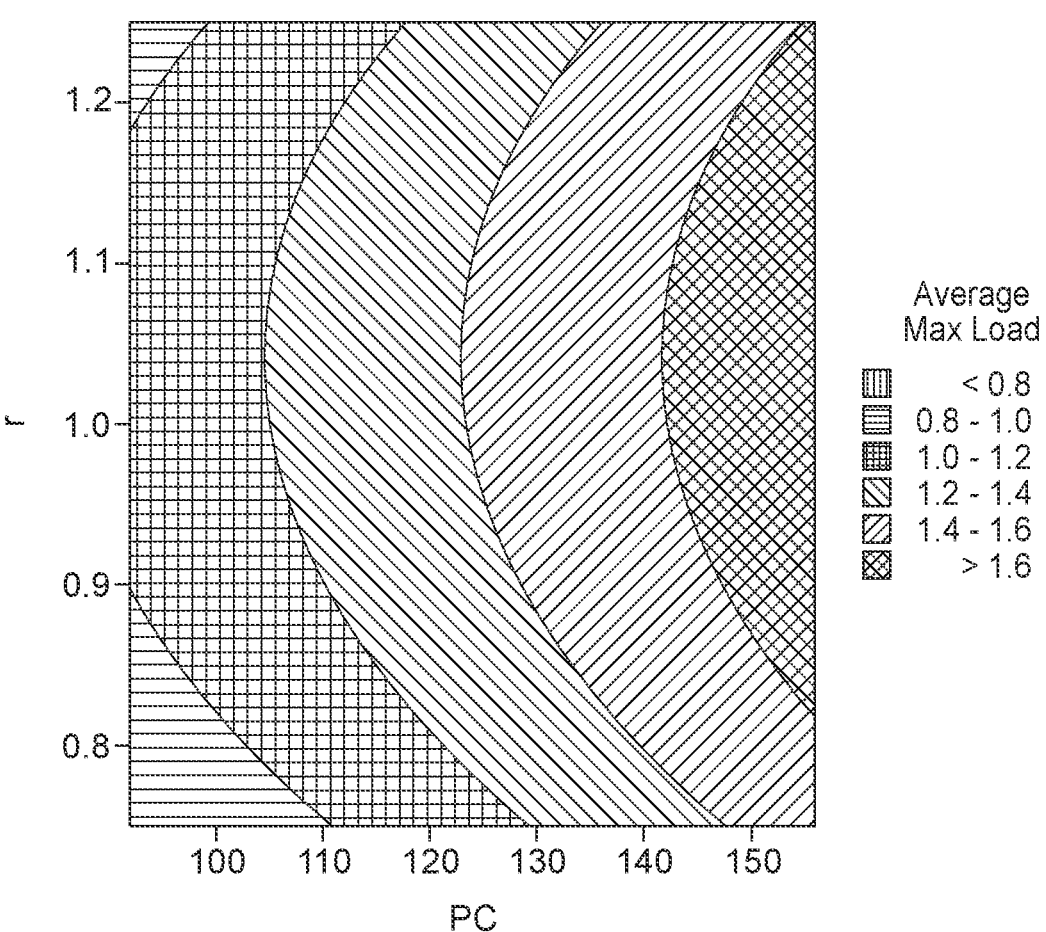
FIG. 3 is a contour plot showing the assessment of average max load at varying ratios (r) of PEG-SG to PEG-Amine, and total polymer content (PC).

In this study, as shown in FIG. 3, tensile maximum (max) load was observed to increase linearly with increasing polymer content and a quadratic effect of r was observed with a maximum near r=1.0, or an even concentration of PEG-SG and PEG-Amine.

Figure 4:
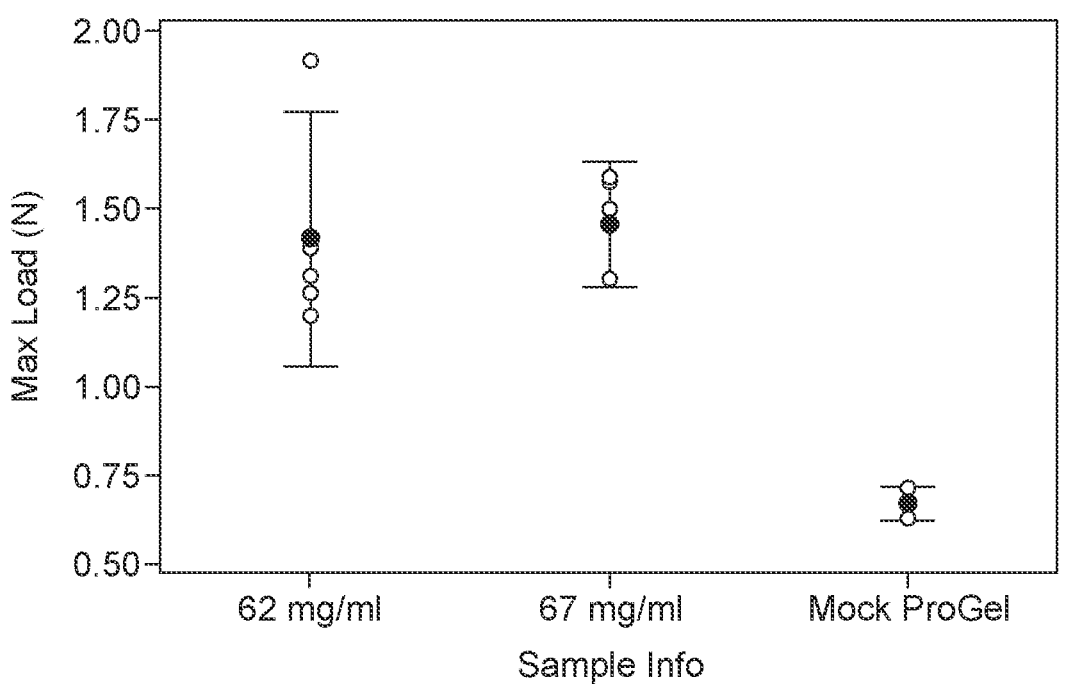
FIG. 4 is a graph showing a tensile max load assessment of two PEG candidates of the invention (Candidate #1: 62 mg/mL PEG-SG and 62 mg/mL PEG-Amine, and Candidate #2: 67 mg/mL PEG-SG and 67 mg/mL PEG-Amine), and a simulated PROGEL™ hydrogel formulation ("Mock PROGEL™ hydrogel") prepared based on publicly available information regarding the marketed PROGEL™ hydrogel sealant (65 mg/mL PEG-succinimidyl succinate, 150 mg/mL Human Serum Albumin, 50 mM carbonate (pH=9.0)). The tensile max load of the lung sealants of the invention was 2.1× greater than Mock PROGEL™ hydrogel.

As shown in FIG. 4, the stiffness of the sealants of the present invention are very low relative to a mock formulation of a currently marketed sealant. Two candidate sealants of the invention were tested against Mock PROGEL™ hydrogel (65 mg/mL PEG-Succinimidyl Succinate, 150 mg/mL Human Serum Albumin, 50 mM carbonate (pH=9.0)) in a tensile assessment. The tensile max load of the two candidate sealants of the invention was observed to be 2.1× greater than Mock PROGEL™ hydrogel. Individual standard deviations were used to calculate the intervals.

A theoretical analysis of the ultimate tensile stress requirement of a sealant for the human lung was performed. The lung was assumed to be a spherical balloon with an extreme worst-case (male, right lung, 99.99 percentile) volume of 5371 mL and the sealant thickness was assumed as 1 mm. The theoretical calculation for burst pressure was as follows:

$$\text{Burst Pressure} = \frac{2*UTS*\delta}{R}$$

Where UTS is the ultimate tensile stress of the sealant, delta is the thickness of the sealant, and R is the radius of the lung. Applying a safety factor of 3 to a standard pleural pressure of 30 cm H$_2$O, the burst pressure was set to 90 cm H$_2$O. A required ultimate tensile strength of 47.8 kPa was calculated which corresponds to a PEG concentration of 39.5 mg/mL PEG-SG and 39.5 mg/mL PEG-Amine.

Varying concentrations of PEG-SG and PEG-Amine were tested. PEG-SG and PEG-Amine concentrations were each increased in equal ratio from 40 mg/mL to 100 mg/mL. As shown in FIG. 7, there was a significant effect of PEG concentration on shear modulus (p<0.01). Interestingly, the maximum shear modulus was observed to peak between 67-77 mg/mL, with no significant differences from 52-62 mg/mL. There was a sharp decrease in shear modulus below 52 mg/mL and above 77 mg/mL.

As shown in FIG. 8, a polymerization time of less than 25 seconds was observed to correlate with acceptable polymerization mechanics. The lower bound dictated by the mechanical requirement of 39.5 mg/mL had a calculated polymerization time of 21 seconds according to a regression model. The upper bound of 86.5 mg/mL corresponded to 25 seconds polymerization time.

There was significant effect of PEG concentration on polymerization rate (p<0.01). As shown in FIG. 9, the polymerization rate demonstrated a significant peak at 67 mg/mL with a range of about 52 mg/mL to about 77 mg/mL demonstrating a fast polymerization rate with no significant differences.

Integrating the data from the mechanical analyses and polymerization time assessment, final concentrations of each of the PEGs in the lung sealants of the present invention are about 39 to about 87 mg/mL, preferably about 52 mg/mL to about 77 mg/mL and, more preferably, 67 mg/mL. In some aspects, the concentration of the PEGs in the lung sealants of the present invention is about 39 mg/mL to about 87 mg/mL, more preferably about 52 mg/mL to about 77 mg/mL, and most preferably about 67 mg/mL.

Example 3

PEG Irradiation

Gamma and X-ray irradiation studies were performed to assess the ability of the lung sealant PEGs to be sterilized. Irradiation of the PEGs was performed under a nitrogen purge.

The PEGs were dosed separately under ambient conditions in glass vials and subjected to 27.9-29.5 kGy gamma irradiation. The PEG-SG was significantly degraded and did not form a hydrogel when combined with a non-irradiated PEG-Amine. The PEG-Amine lost 30% of its functionality and demonstrated significant crosslinking of the PEG backbones.

A subsequent study was performed in an identical manner, but the vials were pulled to 100 mTorr and purged with nitrogen to 600 Torr and the PEG-Amine was irradiated in the protonated HCl salt form. Relative to ambient conditions, the PEG-SG decrease in functionality was decreased by 4%, the low molecular weight degradants decreased by an order of magnitude, and effectively crosslinked when mixed with PEG-Amine. The PEG-Amine decrease in functionality was reduced by 18% and the chain degradation was reduced as well.

These results suggest that irradiation of the lung sealant PEGs must be done under a low oxygen environment and the PEG-Amine should be in the protonated form to prevent large decreases in functionality.

In order to reduce the adverse effects of the irradiation process on the lung sealant PEGs, two antioxidants, BHT and tocopherol, were added at varying concentrations up to 4000 ppm.

As shown in FIGS. 10A-10D, BHT was added at varying concentrations to test for reduction in adverse effects of irradiation on 4-arm PEG-OH with respect to Mn (number average molecular weight) (FIG. 10A), Mp (molecular weight of the highest peak) (FIG. 10B), Mw (weight average molecular weight) (FIG. 10C), and the polydispersity index (PDI) (FIG. 10D).

There were no significant effects on molecular weight distribution and no relationship with viscosity as a function of BHT concentration. Residual BHT was already present in the PEGs as an oxidation protector at 300 ppm or less. Adding additional BHT did not reduce the effects of the irradiation process on the 4-arm PEG-OH.

As shown in FIGS. 11A-11D, tocopherol was added at varying concentrations to test for reduction in adverse effects of irradiation on 4-arm PEG-OH with respect to Mn (number average molecular weight) (FIG. 11A), Mp (molecular weight of the highest peak) (FIG. 11B), Mw (weight average molecular weight) (FIG. 11C), and the polydispersity index (PDI) (FIG. 11D).

The addition of tocopherol demonstrated a linear decrease in post-irradiation molecular weight distribution as tocopherol concentration was increased up to 1500 ppm and viscosity decreased up to 2000 ppm.

Therefore, a range of 1500-4000 ppm tocopherol added to the multi-arm PEGs is maximally effective to achieve the following benefits:

1) Reduced loss of mechanical performance in uniaxial tension, including ultimate tensile strength and elongation at failure;

2) Increase the maximum acceptable dose of X-ray irradiation; and

3) Decrease the viscosity of the resultant PEG solutions to decrease expression force and improve ease of spraying or dripping the lung sealant composition on the lung tissue.

To further understand the effect of tocopherol on the lung sealant PEGs through the irradiation process, the dose dependent effect X-ray irradiation with 2000 ppm ($\pm$)-$\alpha$-tocopherol (tocopherol) was investigated. The PEGs were analyzed for changes in molecular weight distribution as measured via gel permeation chromatography (GPC), chemical functionality via NMR, polymerization time, and cohesive tensile testing.

As shown in, FIGS. 12A-12D, the changes to Mn (number average molecular weight) (FIG. 12A) and Mp (molecular weight of the highest peak) (FIG. 12B) were relatively small. Mn had a maximum change of 6% and 13% for PEG-SG and PEG-Amine, respectively. Mp demonstrated a maximum change of 13% and 4% for PEG-SG and PEG-Amine, respectively. Mw (weight average molecular weight) (FIG. 12C) demonstrated more significant changes up to 18% and 34% for PEG-SG and PEG-Amine, respectively. However, the changes were less than 10% for each PEG up to 25 kGy and 17% at 35 kGy, suggesting the largest differences are observed above 35 kGy. The polydispersity index (PDI) (FIG. 12D) for PEG-Amine increased to a greater extent than PEG-SG, driven due to both decreases in Mn and increases in Mw.

The dose dependent effect of X-ray irradiation (kGy) on PEG-SG and PEG-Amine functionality wherein 2000 ppm tocopherol was added to each of the PEG-SG and PEG-Amine is shown in FIG. 13. The PEGs were X-ray irradiated at 37.6 kiloGrays (kGy) to 46.8 kGy. There was a significant dose dependent effect of X-ray irradiation on PEG-SG functionality (p<0.01, one-way ANOVA) but no significant effect on PEG-Amine functionality (p=0.11, one-way ANOVA). According to a linear regression, 0.14% functionality is lost for every 1 kGy increase in irradiation for PEG-SG. The maximum loss observed at 46 kGy was 10% for PEG-SG.

Low molecular weight PEG oxidation products were observed in the irradiated samples, although no significant differences were observed (one-way ANOVAs). PEG aldehydes and formates remained below 0.05% up to 37 kGy in the PEG-Amine samples, and in all irradiation doses in PEG-SG samples. As shown in FIG. 14, at 46 kGy, 0.01% aldehydes and formates were observed in the PEG-SG sample, and at 46 kGy 0.01%-0.22% aldehydes and formates were observed in the PEG-Amine sample, yielding an average of about 0.11% for PEG-amine, suggesting the response to irradiation may be more variable at this dose for PEG-Amine.

As shown in FIG. 15, PEG esters remained below 0.15% on average in PEG-SG at all irradiation doses and up to 37 kGy in PEG-Amine. At 46 kGy, 0.21% PEG esters were observed in PEG-Amine and 0.12% PEG esters were observed in PEG-SG, suggesting the response to irradiation may be more variable at this dose for PEG-Amine.

The tocopherol concentration was quantified via HPLC. As shown in FIG. 16, PEG-Amine demonstrated a linear decrease in tocopherol as the irradiation dose was increased up to 37 kGy. At higher doses, the tocopherol concentration decreased to approximately 6% of that in the control sample. PEG-SG demonstrated a more marked decrease in tocopherol with approximately 8% remaining at 37 kGy.

Tocopherol concentration was significantly affected by irradiation dose in PEG-Amine ($p < 0.01$) and PEG-SG ($p < 0.01$, one-way ANOVA). Considering the response up to 37 kGy was linear, a regression was performed to understand the change to tocopherol concentration due to X-ray irradiation. 6.4 ppm and 47 ppm tocopherol were lost for every 1 kGy increase in X-Ray irradiation for PEG-Amine and PEG-SG, respectively.

In terms of cohesive mechanical properties, there was no significant difference observed in percent elongation up to 45 kGy, and in tensile strength and modulus up to 35 kGy.

When assessed in a rheometric polymerization assessment, there was a significant effect of irradiation dose on polymerization time and polymerization rate. However, all irradiation doses tested were not significantly different between groups except 37 kGy, which had a 64.2% longer polymerization time than the control.

Use of about 1500 ppm to about 3000 ppm tocopherol in the lung sealant PEG compositions provided herein is most preferable as that range minimizes the amount of tocopherol required while attaining the full benefit of tocopherol as a radioprotectant. However, concentrations of about 500 ppm to about 4000 ppm tocopherol also have significant favorable effects on PEG molecular weight distribution. The maximum X-ray irradiation dose is most preferably about 35 kGy to about 45 kGy.

Example 4

PEG Particle Size Distribution

The lung sealants provided herein are prepared from PEG powders and buffers. The time required to dissolve the PEG powders was tested to identify desirable particle size ranges. PEGs (JenKem) were sieved to various particle size ranges, dried under vacuum and loaded into a lung sealant applicator device. The PEGs were dissolved in the applicator device by a syringe method: 3 strokes (each stroke represents one cycle of push and pull of the syringe plungers in the device) followed by a swirl method of constant circular swirling for 1 minute. Dissolution was tested spectrophotometrically with barium chloride and potassium iodide at 534 nm.

Two sets of PEG-Amine samples were tested: 1) particle sizes with a controlled maximum value (FIG. 17) and 2) particle sizes with a controlled minimum and maximum range (FIG. 18). Unexpectedly, as shown in FIG. 17, there was a statistically significant increasing extent of dissolution with increasing maximum particle size up to 710 μm, after which the extent did not increase further. The extent of dissolution was 36%, 51%, 83%, and 97% relative to the 1200 μm maximum particle size group for 125, 250, 500, and 710 μm, respectively. Small particles clumped and aggregated and slowed dissolution. A similar trend was observed when comparing particle sizes with a controlled minimum and maximum range. As shown in the graph in FIG. 18, there was a statistically significant increasing extent of dissolution, with the 710 μm-1200 μm range demonstrating the greatest and most preferred dissolution. The extent of dissolution was 67%, 86%, and 87% relative to the 710-1200 μm maximum particle size group for the 125-250 μm range, 250-500 μm range, and 500-710 μm range, respectively.

Two sets of PEG-SG samples were tested: 1) particle sizes with a controlled maximum value (FIG. 19), and 2) particle sizes with a controlled minimum and maximum range (FIG. 20). In lung sealant formulations of the present invention, the PEG-SG can dissolve more easily as the citrate buffer is less concentrated, allowing the PEG-SG to solvate more easily. Similar to PEG-Amine, there was a significant effect of particle size on extent of dissolution. However, as shown in the graph in FIG. 19, for PEG-SG, maximum particle sizes of 500 μm, 710 μm, and 1200 μm were completely dissolved and significantly more dissolved than lower maximum particle sizes (125 μm and 250 μm). Particle sizes of greater than 1200 μm were also tested and were completely dissolved as well. As shown in the graph in FIG. 20, when comparing particle size ranges, there was a statistically significant increasing extent of dissolution up to 500-710 μm after which all groups were completely dissolved. The extent of dissolution was 40% and 86% relative to the 500-710 μm range for the 125-250 μm range and 250-500 μm range, respectively. Lower particle size ranges of PEG-SG resulted in similar phenomena observed with PEG-Amine. However, when particle sizes of 500 μm were present the PEG-SG was completely dissolved.

Particle size has a significant effect on the dissolution rate of the PEGs. Unexpectedly, larger particle sizes result in faster dissolution by decreasing the tendency of the PEGs to aggregate and adhere to the glass vial walls. For PEG-Amine, in a particle size distribution, having particles with a particle size of up to 710 μm or greater, or up to 1200 μm present in a distribution along with smaller particles is most preferred.

For PEG-SG (as it is dissolved in a lower concentration buffer), in a particle size distribution, having particles with a particle size up to 500 μm or greater, or up to 1200 microns, present in a distribution along with smaller particles is most preferred. Lower maximum particle sizes will still eventually be dissolved but will require longer preparation times.

Example 5

PEG-Amine Buffer (Alkaline Buffer)

NHS ester/amine chemistry is commonly performed at pH 7.2 to pH 8.5 to yield stable amide bonds. The most common buffers utilized are phosphate, carbonate-bicarbonate, HEPES, or borate buffers. The pH must be maintained at mildly alkaline pH in order to maintain a sufficient proportion of amines in the deprotonated state. However, as the pH is raised, the hydrolysis rate of the PEG-SG ester increases as well. Therefore, when developing a rapid setting sealant based on this chemistry, one much consider the balance between increasing the reaction rate and the loss of reactivity of the PEG-SG.

Unexpectedly, a commonly used buffer for this chemistry, carbonate buffer, was found to be inadequate for use in methods for making the lung sealants of the present invention. A 100 mM carbonate buffer system was tested in a 28.5 mg/mL 4-Arm PEG-Amine-10K, 75 mg/mL 4-Arm PEG-SG-20K system at varying pH using a 40 degree inclined plane travel distance assessment. It was found that the travel distance was significantly reduced with increasing pH. The travel distance was 236 mm at pH 9.0, 140 mm at pH 10.0, and 85 mm at pH 11.0. As a comparison, fibrin sealants travel about 60 mm in the same assessment. Considering pH greater than 10.5 is considered corrosive, the carbonate buffer system was found to be inadequate to maintain a high enough pH for satisfactory polymerization kinetics due to unacceptable runniness at pH 9.

Other buffer candidates were explored with the goal to minimize the required initial pH of the sealant to avoid any possible corrosive effects. Several buffer candidates were tested for their ability to maintain the pH of the sealant throughout the crosslinking reaction at 9.0±0.5 pH. A methoxy PEG-SG surrogate material was utilized in place of 4-Arm PEG-SG to avoid gelation and allow for continuous measurement of the pH of the reaction when combined with PEG-Amine.

The pH was measured over the course of 10 minutes with 100 mM (final concentration) to determine how well the buffer maintained pH when starting at pH 9. The data demonstrated that borate, CHES, and pyridoxine buffer were acceptable with a range of 9-9.4 pKa.

As shown in Table 1 below, a series of buffer pKas were investigated from 7.2 pKa to 10.3 pKa to understand the appropriate range for NHS ester/amine chemistry. The pH after reconstitution of all the buffers was held constant at pH=9.35. Final PEG-SG and PEG-Amine concentrations of 67 mg/mL were tested.

TABLE 1

| Buffer | pKa |
|---|---|
| Phosphate | 7.21 |
| TAPSO | 7.6 |
| TAPS | 8.4 |
| AMPD | 8.8 |
| TABS | 8.9 |
| CHES | 9.3 |
| Pyridoxine | 9.4 |
| CAPSO | 9.6 |
| Carbonate | 10.3 |

As shown in FIG. 21, the polymerization time was significantly affected by buffer pKa (p<0.01). At pH 9.35, buffers having pKas ranging from 8.8 to 9.4 demonstrated significantly reduced polymerization times than those outside of that range. Buffer pKas of 8.4 and 9.6 demonstrated a rapid polymerization rate as well. A quadratic regression was employed to determine the range of pKas resulting in an acceptable polymerization time. For a polymerization time less than 25 seconds, a pKa buffer range from about 7.9 to about 9.7 is preferred.

This discovery with respect to the buffers for use in making the lung sealants of the present invention is unexpected and contradicts the use of buffers commonly used in sealant formulations. Most marketed sealant products utilizing NHS ester/Amine chemistry utilize phosphate, triethanolamine, carbonate, or a combination of such buffer systems in their formulations. There is typically little discussion of the reasoning for using such buffers, although the choice is likely due to the popularity of these buffers across medical device and pharmaceutical formulations and proven safety data. The inventive lung sealant compositions provided herein include biological buffers having a narrower range of pKas, preferably about 7.9 to about 9.7, and most preferably, about 8.8 to about 9.4.

In addition, to choosing the correct buffer candidate, the pH after reconstitution was considered to optimize the set-up time of the sealant. In this assessment, the polymerization time of the sealant was assessed via a travel distance assessment on a 40-degree inclined plane. It was discovered that when increasing the pH of the buffer system just above the pKa of the system a significant decrease in travel distance was observed. This observation was also consistent in borate buffer (pKa=9.0) and pyridoxine buffer (pKa=9.4). These results suggest that the setting time of the sealant can be significantly decreased by increasing the pH after reconstitution at least 0.05 pH units above the pKa of the buffer.

CHES buffer (pKa=9.3) was tested in a polymerization time rheometric method in a two-part experiment. In the first study, a broad range of pHs were tested from 8.0 to 10.5. It was observed the sealant did not polymerize at pH≤8.5. In addition, as the pH was increased from 9.0 to 10.5, the maximum shear modulus decreased linearly. The polymerization time significantly decreased from 9.0 to 9.5 and did not decrease further. There was a significant effect on polymerization rate due to pH, with the fastest polymerization rate observed at pH=9.5.

In the second experiment, a higher resolution study was performed to evaluate pH 9.05 to 9.8 in 0.15 unit increments. In this study, the maximum shear modulus was observed to decrease approximately 3% with every increase of 0.15 pH units. However, the polymerization time significantly decreased from 9.05 to 9.35 after which there were no significant differences observed. As shown in FIG. 22, the polymerization rate demonstrated the greatest mean value at 9.35, but there were no significant differences from 9.20 to 9.80.

Therefore, the pH of the CHES after PEG-Amine dissolution is preferably about 9.0 to about 10.5, more preferably about 9.20 to about 9.80, and most preferably pH 9.35. As shown in FIG. 23, there was a significant effect on polymerization rate due to both CHES concentration (p<0.01) and pH (p<0.01). There was a significant quadratic effect of pH (p<0.01). The fastest polymerization rates were observed at high CHES concentration and intermediate pH. There was a decrease in polymerization rate as pH increased beyond approximately 9.55.

Example 6

Adherence Assessment

The lung sealant of the invention was compared to Mock PROGEL™ hydrogel for ability to stay in place. In this assessment, 4 mL of sealant was manually sprayed to a 2 cm width target zone at an approximate rate of 2 mL/s on a 40 degree inclined plane. The percent of sealant remaining in the target zone was measured gravimetrically.

A prototype lung sealant formulation of the invention compared to a Mock PROGEL™ hydrogel formulation. The lung sealant formulation tested was 78 mg/mL 4 Arm PEG-AmineHCl-20k, 63 mg/mL 4 Arm PEG-SG-20k, 100 mM CHES (pH=9.35). The Mock PROGEL™ hydrogel formulation was 65 mg/mL Linear PEG-SS-4k, 150 mg/mL Bovine Serum Albumin, 50 mM carbonate buffer (pH=9.0).

Next, a functional burst pressure test was performed to understand how the improved ability to remain in place would affect performance. In this assessment, the formulations tested in the angled adherence assessment were tested here. As shown in FIG. 24, burst pressure testing was performed on a 0° (flat), 30°, and 45° inclined plane on porcine pleura tissue with a 1 mm circular defect. The sealant was sprayed onto the tissue, cured for 10 minutes, and the tissue was pressurized until failure.

Qualitatively, the lung sealant of the present invention was observed to completely cover the target tissue at all angles tested. Mock PROGEL™ hydrogel covered the tissue completely in the 0° inclined plane but at 30° some tissue was exposed and at 45° the majority of the sealant ran off forming a hydrogel as it ran.

Quantitatively, the burst pressure of the lung sealant of the present invention did not significantly change with inclined plane angle. On the other hand, Mock PROGEL™ hydrogel significantly decreased with increasing inclined plane angle, decreasing 77% at 45° relative to the flat condition.

Example 7

PEG-SG Buffer (Mildly Acidic Buffer)

NHS activated esters like PEG-SG, are known to hydrolyze over time. Therefore, PEG-SG must be maintained in the dry powder form until the point of use. The hydrolysis rate is dependent on the solution pH with the half-life decreasing as the pH is increased. The hydrolysis rate must be considered as it dictates the working time, defined as the time from PEG dissolution to application of the sealant.

As shown in Table 3 below, currently marketed products with NHS ester chemistry have relatively short working times. PROGEL™ hydrogel, DURASEAL® dural sealant, ADHERUS® dural sealant, and COSEAL™ surgical sealant include 20, 60, 60, and 120 minutes working times in their instructions for use, respectively. PROGEL™ hydrogel does not use a buffered aqueous solution to dissolve the PEG ester in the sealant formulation. DURASEAL® dural sealant, and ADHERUS® dural sealant, use phosphate buffer systems to extend the working time to 60 minutes, and COSEAL™ surgical sealant uses a phosphate buffer system to extend working time to 120 minutes.

TABLE 3

| | Buffer System | pH | Working Time |
|---|---|---|---|
| PROGEL ™ hydrogel | None | Uncontrolled | 20 |
| DURASEAL ® dural sealant | 3.25 mM Phosphate | 4.0 | 60 |
| ADHERUS ® dural sealant | Phosphate | 6.0 | 60 |
| COSEAL ™ surgical sealant | 0.5 mM phosphate | 6.0 | 120 |

*These values based on publicly available information.

The methods for making the lung sealants provided herein utilize a mildly acidic buffer to maintain the PEG-SG at a mildly acidic pH. The extent of hydrolysis of the PEG-SG was monitored over time using a spectrophotometric assay. Briefly, the PEG-SG was dissolved in the buffer of interest, 10 μL of sample was added to a microplate, and incubated for set periods of time. At each time point, 100 μL of 10×PBS (pH=7.8) was added to the solution to stop further hydrolysis and the absorbance was immediately measured at 260 nm.

As shown in FIG. 25, citrate buffer at pH 3.0, 4.0, 5.0, 6.0, and 7.0 was compared to water (assumed as pH=7.0) via a three-way ANOVA. It was found that citrate buffer significantly reduced the extent of hydrolysis of the PEG-SG by 2.5% relative to water over the course of two hours.

The data supports the rate of hydrolysis of PEG-SG can be minimized by dissolution in a mildly acidic buffer such as citrate buffer at pH 4 to about 6 or up to 7, and as pH is decreased, the hydrolysis rate is also decreased. Most preferred is pH from about 4 to less than 5. This is contrary to earlier teachings suggesting pH 5.0 to 6.0 is optimal.

The concentration of the PEG-SG buffer is also significant as well. The concentration must be high enough to neutralize changes induced by the acidic NHS released by PEG-SG due to hydrolysis, but low enough not to inhibit the polymerization reaction once mixed with the PEG-Amine solution. The citrate buffer concentration has no effect on the polymerization time of the lung sealants up to 12.5 mM. However, higher citrate buffer concentrations of 15 mM lead to an increase in polymerization time. A citrate buffer concentration of about 3.5 mM to about 15 mM is preferable, and about 5.5 to about 12.5 mM citrate concentration is most preferable.

The response optimizer algorithm was run to identify the pre-irradiation concentration and pH that would result in a post-irradiation 8 mM citrate buffer with a pH of 4.92. According to this algorithm, a pre-irradiation citrate buffer of 10.6 mM (pH=4.09) would result in the targeted post-irradiation 8 mM buffer (95% confidence interval: 7.89 to 8.11) with a pH=4.92 (95% confidence interval: 4.91 to 4.93).

Example 8

Irradiation of FD&C Blue #1 Lung Sealant Colorant 20 ug/mL FD&C Blue #1 in water was gamma irradiated at 32.3-33.1 kGy. The absorbance at 628 nm was measured on a non-irradiated control and the irradiated sample. The absorbances measured were 2.734 and −0.031, respectively. The blue color of the solution was lost as a result of the irradiation. Therefore, the colorant should not be added to the buffer.

In a subsequent pre-clinical study, the colorant was added to a vial containing dry PEG-SG and a vial containing dry PEG-Amine. FD&C Blue #1 was dissolved in ethanol at 1 mg/mL. 120 μL was pipetted into each vial (for a final concentration of 20 ug/mL) and dried overnight in a vacuum oven at room temperature. The PEGs were then purged with nitrogen, sealed, and irradiated at 26.9-27.4 kGy. The blue color was maintained in each of the dry PEG compositions after irradiation. Therefore, it is preferable to compound the FD&C Blue #1 into the dry PEG compositions because the color is lost when the colorant is irradiated after adding it to the buffer.

Example 9

FD&C Blue #1 Irradiation Dose Study

There were significant differences in FD&C Blue #1 concentration observed due to X-ray irradiation dose. There were no differences observed up to 15 kGy relative to the non-irradiated control. There was a moderate linear correlation between X-ray irradiation dose and FD&C Blue #1 concentration, which indicated a loss of 6.6 ppm FD&C Blue #1 with every1 kGy increase in irradiation dose. Therefore, the colorant should be overdosed by up to 297 ppm to account for irradiation induced loss of color up to 45 kGy irradiation dose.

Example 10

Lung Sealing Efficacy in Physiological Ex-Vivo Lung Chamber Model

Lung sealing efficacy was tested on porcine lungs in an ex-vivo physiological lung chamber model. A 28.5 mg/mL 4-Arm PEG-Amine-10K, 75 mg/mL 4-Arm PEG-SG-20K, 50 mM carbonate (pH=9.0) lung sealing formulation was tested against Mock PROGEL™ hydrogel. This study was focused on demonstrating lung sealing efficacy and the application of the performed with the tissue in a flat orientation to avoid variation caused by the ability of the sealants to stay in place. 10 mm length, 5 mm depth linear parenchymal defects and staple line air leaks were created resulting in mild to severe air leaks. The lung sealant formulation (n=4) and Mock PROGEL™ hydrogel (n=3) demonstrated 100% sealing efficacy under positive ventilator pressure up to 30 cm $H_2O$. Under negative pressure, the lung sealant formulation demonstrated 100% success but Mock PROGEL™ hydrogel failed on 33% of the linear parenchyma defects and 66% of the staple line air leaks. Mock PROGEL™ hydrogel demonstrated exclusively cohesive failures. Although the lung sealant formulation in this example demonstrated 100% sealing efficacy using a carbonate buffer, unexpectedly, as noted herein carbonate buffers are not preferred for use in the lung sealant formulations of the present invention. Additional studies showed unexpected superior results using an alkaline buffer and mildly acidic buffer.

Example 11

Lung Sealing Efficacy in In-Vivo Model

Lung sealing efficacy was tested in an acute large animal model. A 62 mg/mL 4-Arm PEG-Amine-20K (HCl Salt), 62 mg/mL 4-Arm PEG-SG-20K, 100 mM CHES (pH=9.4) lung sealing formulation of the present disclosure, and control test article Mock PROGEL™ hydrogel were tested. 12 mm length, 5 mm depth linear parenchymal defects and a wedge resection of the left apical lung lobe was performed using an Echelon Flex 50 mm linear stapler. A bubble leak test was performed to characterize the severity of the air leaks at 20 cm $H_2O$. The formulations were applied using an EVICEL applicator with the Airless Spray Accessory. Upon completion of the pre-treatment air leak assessment, the visceral surface of the deflated lung was blotted with dry gauze to remove excess moisture, and then the control Mock PROGEL™ hydrogel formulation or lung sealant formulation of the present disclosure (delivered with a prototype device) was applied to the air leak site and staple line. After the control Mock PROGEL™ hydrogel formulation or lung sealant formulation of the present disclosure was allowed to cure for approximately two minutes, the lung was fully inflated, and bubble tests were performed at 20 and 30 cm $H_2O$ ventilator pressure to assess initial sealing efficacy. The lung sealant of the present disclosure was 100% effective (n=4). Once initial sealing efficacy was achieved, the chest wall was temporarily closed using standard techniques. A thoracic drainage catheter was placed in the pleural space and connected to a Pleur-evac® drainage system to allow for the restoration of negative pressure in the thoracic cavity. Following closure of the incision, each animal was continuously maintained under anesthesia for approximately 3.5 hours; mechanical ventilation was utilized during this time. The lung sealant formulation of the present disclosure demonstrated 100% sealing efficacy under positive ventilator pressure up to 30 cm $H_2O$ (n=4).

Additives, such as, chemotherapeutic agents, growth factors, cytokines, antimicrobials, procoagulant hemostatic agents, antifibrinolytics and combinations thereof may be delivered in the lung sealants of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biodegradable lung sealant comprising:
   a) a first component comprising a first multi-arm PEG and an alkaline buffer solution for reconstituting the first multi-arm PEG;
   b) a second component comprising a second multi-arm PEG and a mildly acidic citrate buffer solution for reconstituting the second multi-arm PEG, the mildly acidic citrate buffer solution having a pH prior to reconstitution of about 4.0 to less than 5.0;
   wherein when components (a) and (b) are combined they produce an adherent and elastic biodegradable lung sealant;
   wherein the first multi-arm PEG is 4-arm PEG-NH2-HCl and the second multi-arm PEG is a PEG-NHS ester; and
   wherein a pKa of the alkaline buffer solution is about 7.9 pKa to about 9.7 pKa.

2. The biodegradable lung sealant of claim 1, wherein the first multi-arm PEG of the first component and the second multi-arm PEG of the second component further comprise an antioxidant.

3. The biodegradable lung sealant of claim 2, wherein the antioxidant is tocopherol.

4. The biodegradable lung sealant of claim 3, wherein the antioxidant is α-tocopherol, β-tocopherol, γ-tocopherol, δ-tocopherol, tocotrienol, or a combination thereof.

5. The biodegradable lung sealant of claim 2, wherein the first multi-arm PEG, the second multi-arm PEG, or both the first multi-arm PEG and second multi-arm PEG further comprise a colorant.

6. The biodegradable lung sealant of claim 5, wherein the colorant is FD&C Blue #1, FD&C Blue #2, FD&C Green #3, FD&C Yellow #6, or a combination thereof.

7. The biodegradable lung sealant of claim 1, wherein the first multi-arm PEG and second multi-arm PEG are each 4-arm PEGs.

8. The biodegradable lung sealant of claim 1, wherein the PEG-NHS ester is 4-arm PEG-succinimidyl glutarate (SG).

9. The biodegradable lung sealant of claim 1, wherein final concentrations of the first multi-arm PEG and the second multi-arm PEG in the biodegradable lung sealant are each about 39 mg/mL to about 87 mg/mL, and wherein the first multi-arm PEG and the second multi-arm PEG have a molecular weight of 20 kDa.

10. The biodegradable lung sealant of claim 9, wherein the final concentrations of the first multi-arm PEG and the second multi-arm PEG are each about 52 mg/mL to about 77 mg/mL, and wherein the first multi-arm PEG and the second multi-arm PEG have a molecular weight of 20 kDa.

11. The biodegradable lung sealant of claim 10, wherein the final concentrations of the first multi-arm PEG and the second multi-arm PEG are each 67 mg/mL and wherein the first multi-arm PEG and the second multi-arm PEG have a molecular weight of 20 kDa.

12. The biodegradable lung sealant of claim 1, wherein the first multi-arm PEG and the second multi-arm PEG are each compounded with about 1500 ppm to about 3000 ppm of an antioxidant.

13. The biodegradable lung sealant of claim 12, wherein the antioxidant is tocopherol.

14. The biodegradable lung sealant of claim 1, wherein the pKa of the alkaline buffer solution is about 8.8 pKa to about 9.4 pKa.

15. The biodegradable lung sealant of claim 1, wherein a pH after reconstitution of the alkaline buffer solution is at least 0.05 pH units above a pKa of the alkaline buffer solution.

16. The biodegradable lung sealant of claim 15, wherein the pH after reconstitution of the alkaline buffer solution is about 9.0 to about 10.5.

17. The biodegradable lung sealant of claim 1, wherein the mildly acidic buffer solution has a concentration of about 3.5 mM to about 15 mM.

18. The biodegradable lung sealant of claim 1, wherein the second multi-arm PEG is 4-arm PEG-SG, and wherein the biodegradable lung sealant further comprises tocopherol and FD&C Blue #1, and wherein, after combining the components, the biodegradable lung sealant comprises 67 mg/mL 4-arm PEG-SG, 67 mg/mL 4-arm PEG-NH2-HCl, 340 µg/mL tocopherol, and 80 µg/mL FD&C Blue #1.

19. The biodegradable lung sealant of claim 1, further comprising a contrast agent.

20. A method of using the biodegradable lung sealant of claim 1 comprising: adding tocopherol to the 4-arm PEG-Amine to form a 4-arm PEG-Amine and tocopherol mixture; irradiating the 4-arm PEG-Amine and tocopherol mixture; adding the alkaline buffer to the 4-arm PEG-Amine and tocopherol mixture to form the first component of the lung sealant; adding tocopherol to the 4-arm PEG-NHS ester to form a 4-arm PEG-NHS ester and tocopherol mixture; irradiating the 4-arm PEG-NHS ester and tocopherol mixture; adding the mildly acidic buffer to the 4-arm PEG-NHS ester and tocopherol mixture to form the second component of the lung sealant; and using an applicator device to mix and simultaneously apply the first component and second component onto a lung tissue to form the lung sealant, and allowing the sealant to cure on the tissue.

21. The method of claim 20, wherein the 4-arm PEG-Amine and tocopherol mixture, and 4-arm PEG-NHS ester and tocopherol mixture are each irradiated with X-ray irradiation up to about 40 kiloGrays (kGy).

22. The method of claim 20, wherein each of the 4-arm PEG-Amine and 4-arm PEG-NHS ester are irradiated under a low oxygen environment and the 4-arm PEG-Amine is in a protonated form.

* * * * *